United States Patent [19]

Hider et al.

[11] Patent Number: 4,912,118

[45] Date of Patent: * Mar. 27, 1990

[54] PHARMACEUTICAL COMPOSITIONS

[75] Inventors: Robert C. Hider, Clacton; George Kontoghiorghes; Jack Silver, both of London; Michael A. Stockham, Saffron Walden, all of England

[73] Assignee: National Research Development Corporation, London, England

[*] Notice: The portion of the term of this patent subsequent to Apr. 29, 2006 has been disclaimed.

[21] Appl. No.: 944,872

[22] Filed: Dec. 22, 1986

Related U.S. Application Data

[62] Division of Ser. No. 651,684, Sep. 18, 1984, Pat. No. 4,666,927.

[30] Foreign Application Priority Data

Sep. 23, 1983 [GB] United Kingdom ............... 8325494

[51] Int. Cl.$^4$ .................. C07D 401/12; C07D 401/14
[52] U.S. Cl. .................................... 514/332; 514/334
[58] Field of Search ............... 514/332, 334, 348, 350, 514/352; 424/10, 147

[56] References Cited

U.S. PATENT DOCUMENTS

| | | |
|---|---|---|
| 2,429,096 | 10/1947 | Ladd et al. |
| 2,686,786 | 8/1954 | Shaw et al. |
| 2,742,476 | 4/1956 | Bernstein et al. |
| 2,748,142 | 5/1956 | Clauson-Kass ........................ 546/243 |
| 3,269,904 | 8/1966 | Bernstein ............................. 514/345 |
| 3,419,570 | 12/1968 | Brammer ............................. 546/250 |
| 3,705,943 | 12/1972 | Kaufman ............................. 514/188 |
| 3,810,752 | 5/1974 | Wilcox et al. |
| 3,847,927 | 11/1974 | Dunbar ............................. 546/294 |
| 3,864,334 | 2/1975 | Pallos |
| 3,928,616 | 12/1975 | Pallos |
| 3,963,729 | 6/1976 | Gittas ............................. 544/85 |
| 3,968,118 | 7/1976 | Lohaus ............................. 546/296 |
| 4,063,927 | 12/1977 | Otten et al. |
| 4,143,131 | 3/1979 | Lindenbaum ....................... 424/2 |
| 4,181,654 | 1/1980 | Weitl ............................. 540/474 |
| 4,293,542 | 10/1981 | Lang et al. |
| 4,309,305 | 1/1982 | Weitl et al. ...................... 423/8 |
| 4,358,455 | 11/1982 | Atkinson et al. |
| 4,396,766 | 8/1983 | Farmer, Jr. et al. |
| 4,397,867 | 8/1983 | Blake ............................. 424/320 |
| 4,419,365 | 12/1983 | McLachlan ....................... 424/320 |
| 4,442,305 | 4/1984 | Weitl ............................. 562/451 |
| 4,530,963 | 7/1985 | DeVoe et al. .................... 525/54.1 |
| 4,543,213 | 9/1985 | Weitl ............................. 540/474 |
| 4,585,780 | 4/1986 | Hider ............................. 514/348 |
| 4,698,431 | 10/1987 | Raymond et al. ................. 546/298 |

FOREIGN PATENT DOCUMENTS

| | | |
|---|---|---|
| 0093498 | 11/1983 | European Pat. Off. |
| 0094149 | 11/1983 | European Pat. Off. |
| 0105053 | 4/1984 | European Pat. Off. |
| 2555411 | 6/1976 | Fed. Rep. of Germany |
| 2808825 | 9/1978 | Fed. Rep. of Germany |
| 2721888 | 11/1978 | Fed. Rep. of Germany |
| 3005069 | 8/1981 | Fed. Rep. of Germany |
| 42-23195 | 11/1967 | Japan |
| 53-98972 | 8/1978 | Japan |
| 58-32812 | 2/1983 | Japan |
| 162003 | 4/1964 | U.S.S.R. |
| 0778871 | 7/1957 | United Kingdom |
| 1416397 | 12/1957 | United Kingdom |
| 790584 | 2/1958 | United Kingdom |
| 791719 | 3/1958 | United Kingdom |
| 1238106 | 7/1971 | United Kingdom |
| 1446409 | 8/1976 | United Kingdom |
| 1593822 | 7/1981 | United Kingdom |
| 2117766 | 10/1983 | United Kingdom |
| 2118176 | 10/1983 | United Kingdom |

OTHER PUBLICATIONS

Itoh et al., "The Journal of Antibiotics", XXXII, No. 11, pp. 1089–1095, (Nov. 1979).
Barker et al., Chemical Abstracts, vol. 92, No. 21, May 26, 1980, p. 476, Abstract No. 179021g and Journal of Antibiotics, vol. 32, No. 11, 1979.
McInnes et al., Journal of the Chemical Society, Chemical Communications, 1974, No. 8, 218–282.
Neilands, Science, 1967, 156, 1443–1447.
Dittmar et al., 1974, 17, 753–756.
Durbin, P. W. et al., "Kinetics of Plutonium Deposition in the Mouse", Ann. Rpt. 1983-4, Biology and Medicine Division, Lawrence Berkeley Lab. (Apr. 1985).
Durbin, P. W. et al., "New Sequestering Agents for the Actinides . . . ", Ann Rpt. 1983-4, Biology and Medicine Division, Lawrence Bereley Lab., (Apr. 1985).
Raymond, K. N., "Specific Sequestering Agents for Iron and Actinides", in *Environmental Inorganic Chemistry*, (VCH Publishers, Inc. 1985).
Riley, P. E. et al., "Specific Sequestering Agents for the Actinides, 9, Synthesis of Metal Complexes of 1-Hydroxy-2-Pyridinone . . .", *Inorganic Chemistry*, 22 (1983), p. 3940 et seq.
Scarrow, R. C. et al., "Ferric Ion Sequesting Agents . . .", *Inorganic Chemistry*, 24, (1985), p. 954 et seq.
Scarrow et al., CA 102:124493g.
Raymond et al., CA 103:192911n, European Search Report.
Chemical Abstracts, vol. 93, No. 13, 29 Sep. 1980, pate 504, col. 2, Abstract No. 130476r is an abstract of ref. 1 above, Itoh et al.
WPIL Print out re: U.S. Pat. No. 4,587,240.
Chemical Abstracts, vol. 93, No. 13, 09/29/1980, p. 504, col. 2, Abstract No. 130476r.

(List continued on next page.)

Primary Examiner—Christopher Henderson
Attorney, Agent, or Firm—Oblon, Spivak, McClelland, Maier & Neustadt

[57] ABSTRACT

Compounds in which two or more rings, being a 3-hydroxpypyrid-2-one, 3-hydroypyrid-4-one or 1-hydropyrid-2-one, are linked are of value in the treatment of patients having a toxic concentration of a metal, particularly iron, in the body while the iron complexes of such compounds are of value in the treatment of iron deficien 23 Claims, No Drawings

OTHER PUBLICATIONS

Chemical Abstracts, vol. 64, No. 3, 01/31/1966, col. 3504.
Pitt et al., "The Design and Synthesis of Chelating Agents for the Treatment of Iron Overload in Colley's Anemia", Research Triangle Institute, DHEW....
Tamhina et al., "Extraction and Spectrophotometric Determination of Iron (III) by 1-Phenyl-2-Methyl-3-Hydroxy-4-Pyridone", *Croatica Chemica Acta* CCACAA 45....
Berson et al., "Spectra as a Guide to Structure in the Hydroxypyrone and Hydroxypyridone Series", Dept. of Chemistry, University of Southern....
Jacobs, "Screening for Iron Chelating Drugs", Elsevier North Holland, Inc., 1981, pp. 39–46, This publication discusses various drugs useful for iron....
Wilson et al., "Chelation and Biologic Action, Textbook of Organic Medicinal and Pharmaceutical Chemistry", Third Edition, J. B. Lippincott Company....
CA 90:186151m, This document discloses 6-substituted 3-hydroxy-1-methyl-4-pyridones.
CA: 90:167745s, This document discloses 5-hydroxy-2-(hydroxymethyl)-4-pyridones.
CA 89:37739m, This document discusses the comparative toxicities of mimosine and some chemically related compounds, including 3-hydroxy-4-(1H)-pyridone.
CA 86:167059p, This document discloses the inhibition of copper-containing enzymes by L-mimosine, discussing the effect of $Fe^{3+}$ or $Cu^{2+}$ on this process.
CA 85:104644j, This document discloses the inhibition of wool folicle DNA synthesis by minosine and related 4(1H)-pyridones.
CA 80:103826e, This document discloses aromatic amino acid hydroxylase inhibitors repaired by oxidation of kojic acid benzylether to the pyrone....
CA 77:122732a, This document discloses that mimosinamine dihydrochloride results in complete loss of hair of suckling mice, and that this effect....
*J. Med. Chem.*, (1974), vol. 17, No. 1, pp. 1–5, "Aromatic Acid Hydroxylase Inhibitors...".
CA 86:12119e, This document discloses the synthesis of some 4-pyranones and 4-pyridones.
*Bull. Chem. Soc. Japan*, 52, No. 1, Jan. 1979, p. 107, K. Imafuku et al., This document discloses the preparation of 5-hydroxy-2-hydroxymethyl-4-pyridone....
CA 85:143377u, This document discusses the formation of pyridone derivatives from maltose and lactose.
*Z. Lebensm. Unters. Forsch.*, T. Severin et al., 1976, This document discloses formation of pyridone derivatives from maltose and lactose.
CA 76:71652u, This document discusses the orientation of the aminomethylation of 2,5-dihydroxypyridine and N-methyl-3-hydroxy-2-pyridone.
*J. Med. Chem.*, (1979), vol. 22, No. 1, This document discloses aromatic amino acid hydroxylase inhibitors which are azadopamine analogs.
CA 74:23102b, This document discloses the synthesis of N-substituted-3-glucosyloxy-2-methyl-4-pyridones and their aglycones.
CA 97:92048a, This document discloses the synthesis and structure of heterocyclic compounds with chelating properties, including maltol.

*Bull. Chem. Soc. Japan*, 52, No. 1, Jan. 1979, p. 111, K. Imafuku et al., This document discloses the preparation of various 6-substituted 3-....
*Inorg. Chem.* (1985), 24, pp. 954–967, This paper investigates a range of liganda and identifies the 3-hydroxypyrid-4-ones as being of particular....
*J. Chem. Soc., Dalton Trans.*, (1982), pp. 1433–1438, This paper relates to the iron complexes of two pyridine derivatives, one of which, 2,3-....
*The Lancet* (Jun. 6, 1987), pp. 1294–1295, This paper illustrates the value of 3-hydroxy-1,2-dimethylpyrid-4-one.
Porter et al., "The Relationship Between ...", This paper relates to the value of hydroxypyrid-4-one iron chelators in the treatment of iron overload.
Gyparaki et al., "In Vivo Evaluation of ...", This paper relates to the value of a hydroxypyrid-4-one iron chelators in the treatment of treatment of iron....
*Bol. Soc. Chil. Quim.*, 1982, p. 27, 122, This document discloses certain N-alkyl-3-hydroxypyrid-4-one, These are described in the context of their....
*Chem. Pharm. Bull.*, 1980, 28, pp. 28, 2570–2579, This paper describes tests on certain hydroxypyridones which are substituted by an alkyl group at a....
*Aust. J. Bol. Sci.*, 1978, 31, p. 115, This paper describes test for cytotoxic activity on various hydroxypyridones.
*Can. J. Chem.*, 1976, 54, p. 3377, This paper refers to the testing of various compounds, including a N-substituted hydroxypyridone containing....
Pitt et al., "The Design and Synthesis ...", Research Triangle Institute, Research Triangle Park, N.C., (1975), this paper provides a....
*Aust. J. Bol. Sci.*, 9176, 29, p. 189, This paper relates to studies on certain metal-free hydroxypyridones as inhibitors of wool folical DNA....
*Croatica Chemia Acta* CCACAA, 1973, 45, p. 603, This paper is concerned with the use of a hydroxypyridone N-substituted by an aromatic group in....
*Yakugaku Zasshi*, 1970, 90, p. 1222, This document discloses the synthesis of N-substituted 3-glucosyloxo-2-methyl-4-pyridones, This aglycones, ....
*J. Bacteriol.*, (1973), 141 (1), 164–168), This document relates to a variety of compounds, including hydroxypyridones which are siderophores for the ...
*Recueil* (1950), pp. 1041–1047, this document describes the preparation of various N-alkyl-3-hydroxypyrid-4-ones, such as the N-propyl-3-....
*J. Med. Chem.*, (1973), vol. 16, No. 5, pp. 581–583, This document reports preliminary results of a study on the in vitro inhibition of the enzyme....
*Tox. Appl. Pharm.*, (1969), 14, pp. 249–258, This document discloses studies of the effect of 1,3-disubstituted 2- and 6-pyridones on the functioning....
*Bull. Chem. Soc. Japan*, (1979), vol. 52 (1), pp. 111–113, this document reports studies on the effect of substituents on physical properties of....
*Z. Lebensm, Unters.-Forsch.*, (1976), 161, pp. 119–124, this document discloses the preparation of N-methyl-3-hydroxy-2-methylpyrid-4-one, no reference...

(List continued on next page.)

OTHER PUBLICATIONS

*Rec. Trav. Chem.*, 65:65 (1946), This document relates to the determination of the structure of the N-methyl-3-hydroxypyrid-2-one, it also discloses. . . .

*Helvetica Chimica Acta.*, vol. XXIX, Fasciculus VII (1946), pp. 1669–1675, This document refers to the structure of the N-methyl-3-hydroxy-4-one. . . .

*Tetrahedron,* (1970), vol. 26, pp. 3779–3785, This document describes the preparation of the N-methyl-3-hydroxypyrid-2-one, it also describes. . . .

*J. Chem. Soc.*, (1947), 69:1801, This document describes the compounds N-methyl and N-ethyl-3-hydroxy-4-one, in the formation of a coloration and in. . . .

*J. Bacterol.*, (1980), 141(1), pp. 164–168, "Identification of the Thujaplicina . . . ", This document relates to a variety of compounds. . . .

Jacobs, "Screening for Iron Chelating Drugs", (1981), This document is a general review of the screening of drugs for iron chelation therapy.

*J. Pharm. Sci.*, vol. 68, No. 7, p. 816, (1979), This document discloses pyridones as potential antitumor agents.

CA 94:65438j, This compound discloses pyridones as potential antitumor agents, 4-pyridones and bioisosteres of 3-actoxy-2-pyridone.

Goodman and Gilman's "The Pharmacological Basis . . . ", This document discloses the sequence of steps in enzymatic synthesis of dopamine, norepinephrine. . . .

CA 85:143377u, This document discusses the formation of pyridone derivatives for maltose and lactose.

CA 92:146042m, This document discloses the oxidation of N-methyl-3-pyridone to 3-hydroxy-N-methyl-2-pyridone.

CA 94:76572z, This document discloses the antithyroid and antiperoxidase activity of some isomeric dihydroxy pyridines.

*Chem. Pharm. Bull.* 28(9) pp. 2570–2579 (1980), This document discloses the central depressant effect of maltol analogs in mice.

CA 97:92048a (1982) Bartulin et al.
CA 74, No. 5 (1971) Yasue et al.
CA 79, No. 15 (1973) Borchardt.
CA 73, No. 21 (1970) Moehrle.

*J. Pharm. Sci.* (Sep. 1980), vol. 69, No. 9, p. 1074, This document discloses pyridones as being potential anti-tumor agents.

Wilson et al., "Textbook of Organic Medicinal and Pharmaceutical Chemistry", 3rd Edition, pp. 25–27, Lippincott Pub. (1956), This document describes. . . .

*Inorg. Chem.* (1983), pp. 480–485, This document discusses the stability of metal complexes, The discussion on p. 482 relates the advantages. . . .

*J. Polym. Sci.:* Pol. Chem. Ed. (1976), vol. 14, pp. 2155–2165, This document discloses the iron chelating ability of hydroxamic acid polymers, for. . . .

*J. Am. Chem. Soc.* (1979), vol. 101, pp. 6534–6541, This paper describes ferric iron sequestering agents, for potential medical use, which. . . .

*J. Med. Chem.* (1979), vol. 22, pp. 1281–1283, This document describes ferric iron sequestering agents, for potential medical use, which contain. . . .

*J. Med. Chem.* (1980), vol. 23, pp. 1130–1133, This paper describes ferric iron sequestering agents, for potential medical use, which contain two. . . .

*Ann. N.Y. Acad. Sci.* (1981), pp. 425–435, This document is a review of iron chelators for medical use.

*Tet. Lett.* (1981), vol. 22, pp. 2739–2742, This document describes iron (III) chelators, for potential medical use, consisting of a randon complex. . . .

*In. Chem.* (1982), vol. 21, pp. 2209–2215, This document discloses gallium in indium complexes of compounds containing three linked sulfonated. . . .

*J. Am. Chem. Soc.* (1981), vol. 103, pp. 5133–5140, This document describes ferric iron sequestering agents, for potential medical use, which. . . .

*In. Chem.* (1982), vol. 21, pp. 3437–3442, This document discloses compounds containing two, three or four linked sulfonated catechol groups in the. . . .

*Biochem.* (1983), vol. 22, pp. 1621–1630, This document describes the attachment of ethylene diamine chelators to a polymer support to provide. . . .

*J. Pharm. Exp. Therap.* (1984), vol. 228, pp. 676–781, This document describes studies on iron chelators, for potential medical use, consisting of. . . .

*Rad. Research* (1984), vol. 99, pp. 85–105, This document describes the use of compounds containing two, three or four linked sulfonated catechol groups. . . .

CA 69:35956t.
CA 69:35967x.
CA 69:35968y.
CA 72:12596y.
CA 72:132534y.
CA 72:132537b.

*Ann. Rep. Shionogi Research Lab.* (1966), vol. 16, pp. 29–40, This document discloses a range of substituted 2-hydroxypyridine 1-oxide compounds. . . .

*J. Am. Chem. Soc.* (1949), vol. 71, pp. 67–73, This document discloses a range of substituted 1-hydroxypyrid-2-one compounds, including the 4-methyl. . . .

*In. Chim. Acta.* (1981), vol. 51, pp. 109–115, This document reports the preparation of various metal complexes of the unsubstituted. . . .

*In. Neucl. Chem. Lett.* (1979), vol. 15, pp. 255–258, The cobalt(II) and cobalt (III) complexes of 1-hydroxypyrid-2-one were prepared and studied. . . .

Pitt et al., "Development of Iron Chelators for Clinical Use" (1975), p. 137, This paper provides a discussion of alternative types of chelating agents. . . .

PHARMACEUTICAL COMPOSITIONS

This is a division of application Ser. No. 651,684, filed Sept. 18, 1984, now U.S. Pat. No. 4,666,927.

This invention relates to compounds for use in pharmaceutical compositions.

Certain pathological conditions such as thalassaemia, sickle cell anaemia, idiopathic haemochromatosis and aplastic anaemia are treated by regular blood transfusions. It is commonly found that such transfusions lead to a widespread iron overload, which condition can also arise through increased iron absorption by the body in certain other circumstances. Iron overload is most undesirable since, following saturation of the ferritin and transferrin in the body, deposition of iron can occur and many tissues can be adversely affected, particular toxic effects being degenerative changes in the myocardium, liver and endocrine organs. Such iron overload is most often treated by the use of desferrioxamine. However, this compound is an expensive natural product obtained by the culture of Streptomyces and, as it is susceptible to acid hydrolysis, it cannot be given orally to the patient and has to be given by a parenteral route. Since relatively large amounts of desferrioxamine may be required daily over an extended period, these disadvantages are particularly relevant and an extensive amount of research has been directed towards the development of alternative drugs. However, work has been concentrated on three major classes of iron chelating agents or siderophores, namely hydroxamates, ethylenediamine tetra-acetic acid (EDTA) analogues and catechols. The hydroxamates generally suffer from the same defects as desferrioxamine, being expensive and acid labile, whilst the other two classes are ineffective at removing iron from intracellular sites. Moreover, some cathechol derivatives are retained by the liver and spleen and EDTA analogues possess a high affinity for calcium and so are also likely to have associated toxicity problems.

We have accordingly studied the iron chelating ability of a wide range of compounds and in UK patent application Nos. 8308056 (published as GB No. 2118176A), 8407181 (published as GB No. 2136807A), and 8423800 (published as GB No. 2146990A), as well as in corresponding applications filed overseas (European application Nos. 83301659.5 and 84301881.3, Greek application Nos. 70868 and 74187, Japanese application Nos. 83/049676, and 84/057185, U.S. application Ser. Nos. 478493, now continuation application Ser. No. 933338, and 592271 (corresponding to U.S. Pat. No. 4,585,780), and a further copending application in our name of even date herewith filed in each of Europe, Greece, Japan and the U.S.A. (Application Ser. No. 651,772; U.S. Pat. No. 4,587,240) claiming priority from UK application No. 8325496), we described certain compounds which we have identified as being of particular use for the treatment of conditions involving iron overload. These compounds consists of 3-hydroxypyrid-2-ones and 3-hydroxypyrid-4-ones having a substituent on the nitrogen atom and optionally also on one or more of the carbon atoms of the ring, and 1-hydroxypyrid-2-ones which are substituted on one or more of the carbon atoms of the ring. We have now found that compounds containing two or more linked 3-hydroxypyrid-2-one, 3-hydroxypyrid-4-one or 1-hydroxypyrid-2-one rings are of significant value in the treatment of iron overload.

Accordingly the present invention comprises a compound in which two or more rings, being a 3-hydroxypyrid-2-one, 3-hydroxypyrid-4-one or 1-hydroxypyrid-2-one, are linked.

The hydroxypyridone rings in compounds according to the present invention may be identical or may differ, either varying between the three forms of hydroxypyridone and/or, since the ring may be substituted, between differing rings of the same basic form. In general, however, there is little advantage to be gained from the presence of dissimilar rings and this can complicate the synthesis of the compound so that it is preferred that each hydroxypyridone ring in the compound is of the same one of the three forms and conveniently that each ring possesses the same substitution or lack of substitution.

Although compounds according to the present invention may contain varying numbers of rings, for example up to 10 or even 100, compounds containing 2, 3 or 4 rings are of particular interest with the 3 ring compounds being of especial use in the treatment of conditions involving iron overload.

The ability of both the free compound and its iron complex to permeate membranes is important in the context of the treatment of iron overload, and it is also desirable for both to possess some degree of water solubility. A good indication of the physical properties of a compound and its iron complex in this respect is provided by the value of the partition coefficient ($K_{part}$) obtained on partition between n-octanol and tris hydrochloride (20 mM, pH 7.4; tris representing 2-amino-2-hydroxymethylpropane, 1,3-diol) at 20° C. and expressed as the ratio (concentration of compound in organic phase)/(concentration of compound in aqueous phase). Where the compounds are to be employed in a context requiring translocation across membranes, then preferred compounds show a value of $K_{part}$ for the free compound of above 0.02 but less than 3.0, especially of above 0.2 but less than 1.0, together with a value of $K_{part}$ for the smallest neutral iron(III) complex in which there is an internal balance of charges of above 0.02 but less than 6.0, especially of above 0.2 but less than 1.0. [In a neutral complex there is an internal balance of charges between the iron cation or cations and the ligand or ligands covalently bound thereto without the necessity for the presence of a non-covalently bound ion or ions to achieve balance. In the case of two ring compounds, for example, this smallest neutral iron(III) complex will contain 3 molar proportions of the compound:2 molar proportions of iron (III) but for the preferred iron binding compounds containing three rings the complex will contain a 1:1 molar ratio of compound:iron(III).] In other contexts, such as the intraveneous use of the compounds in vivo, the value of $K_{part}$ is less critical. The comments which follow later upon preferred forms of linking groups are in part directed towards providing compounds having partition coefficients in the free and complexed state which lie in the preferred ranges indicated above, which preferences as to linking groups also apply broadly to compounds for use in the removal of the other metals from the body as discussed hereinafter although the preferred number of rings present in the compound may then be different.

The hydroxypyridone rings may, for example, be substituted as discussed in the aforementioned UK patent applications for the single ring compounds, allowing for the necessity to provide a point of linkage for the various rings so that, for example, if the rings are linked through the nitrogen atoms thereof then this position of the ring may not be otherwise substituted.

Examples of types of substitution additional to the linking groups thus include, for 3-hydroxypyrid-2-one and 3-hydroxypyrid-4-one rings replacement of the hydrogen atom attached to the nitrogen atom by an aliphatic acyl group, by an aliphatic hydrocarbon group, or by an aliphatic hydrocarbon group substituted by one or, except in the case of ionisable groups, more than one substituent selected from aliphatic acyl, alkoxy, aliphatic amine, aliphatic amide, carboxy, aliphatic ester, halogen, hydroxy and sulpho groups and/or replacement of one or more of the hydrogen atoms attached to ring carbon atoms by one of said substituents, by an aliphatic hydrocarbon group, or by an aliphatic hydrocarbon group substituted by an alkoxy, aliphatic ester, halogen or hydroxy group; and for 1-hydroxypyrid-2-one rings, replacement of one or more of the hydrogen atoms attached to ring carbon atoms by a substituent selected from aliphatic acyl, aliphatic amide, aliphatic amine, carboxy, cyano, aliphatic ester, halogen, hydroxy and sulpho groups, alkoxy groups and alkoxy groups substituted by an alkoxy, aliphatic amide, aliphatic amine, aliphatic ester, halogen or hydroxy group, aliphatic hydrocarbon groups and aliphatic hydrocarbon groups substituted by an alkoxy, aliphatic ester, halogen or hydroxy group.

Further description of such substituents as are listed above is to be found in the earlier applications referred to hereinbefore but it may be mentioned that the ionisable substituent groups are generally of lesser interest than the others and, indeed, substitution of the rings other than for the purpose of the linkage thereof is of much less interest than in the case of the single ring compounds. Since, as will be discussed in more detail hereinafter, the 3-hydroxypyrid-2- and -4-one rings are preferably linked through the nitrogen atoms thereof and the hydroxy group on the nitrogen atoms of the 1-hydroxypyrid-2-ones is required for iron binding, such substitution as is present is more usually limited to the carbon atoms of the ring and is preferably limited to aliphatic hydrocarbon substituent groups. Moreover, although more than one of the ring carbon atoms may be substituted, for example two of such atoms, either by the same or different substituent groups, compounds in which only one, or none, of the ring carbon atoms are substituted are preferred. Substitution may occur at various positions of the ring but, particularly when the ring carbon atoms are substituted by the larger groups, there may be an advantage in avoiding substitution on a carbon atom alpha to the

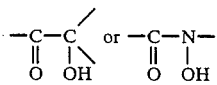

system. These systems are involved in the complexing of the compound with iron and other metals and the close proximity of one of the larger groups may lead to steric effect which inhibit complex formation.

Where a ring is substituted by an aliphatic hydrocarbon group, this group may be cyclic or acyclic, having a branched chain or especially a straight chain in the latter case, and may be unsaturated or especially saturated. Groups of from 1 to 6 carbon atoms, particularly of 1 to 4 and especially of 1 to 3 carbon atoms, are of most interest. Alkyl groups are preferred, for example cyclic groups such as cyclopropyl and especially cyclohexyl but, more particularly preferred are acyclic groups such as methyl, ethyl, n-propyl and isopropyl. The main interest in aliphatic hydrocarbon group substituents in the context of the present invention lies, however, in the possibility of using single ring compounds containing such a substituent on one or more carbon atoms thereof as being a more readily available starting material than the corresponding unsubstituted compound for the preparation of the multi-ring compounds. In this respect, methyl substituent groups are of particular interest and have the advantage of not being so large as to create the problems referred to above. Thus, with the 3-hydroxypyride-4-ones, where the use of methyl substituted compounds as starting materials is of most relevance, it is likely, for reasons of availability, that any methyl substituent will in fact be located at the 2- or 6-position.

Preferred ring systems present in the compounds of the present invention are shown below, the free valency in each case indicating the preferred point of attachment of the linking group between one ring and another (it will be appreciated that the 1-hydroxypyrid-2-ones are tautomeric compounds, being alteratively named as 2-hydroxypyridine-1-oxides).

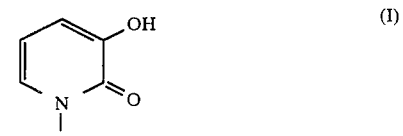

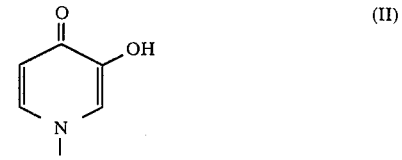

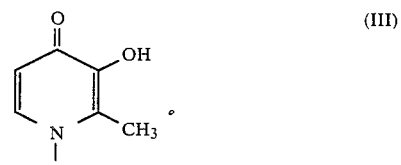

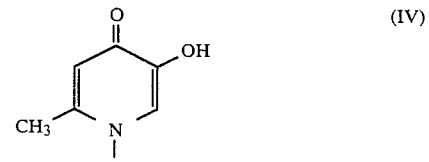

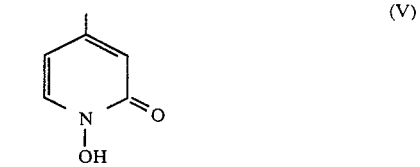

The hydroxypyridone rings may be linked through various types of linking group, the important feature of the compounds being the rings contained therein and the nature of the linking groups therefore being of lesser importance. From the point of view of ease of synthesis and non-interference in the metal complexing action of the compounds, however, it is preferred to use linking groups which are either wholly of a hydrocarbon nature or which additionally contain one or more of the same or different groups such as —O—, —S—, —NH—,

—CONH—,

etc.

For reasons of simplification of the description only, the preparation of compounds according tot he present invention will be further described with particular reference to the preparation of two ring and three ring compounds.

Examples of suitable linking hydrocarbon linking groups are a benzene group substituted by two or more methylene groups, and various aliphatic hydrocarbon groups. The latter may conveniently contain between 6 and 18 or 24 carbon atoms, especially between 6 or 8 and 12 carbon atoms, and when used in two ring compounds, where they are particularly useful, are preferably straight chain alkylene groups, although when used in compounds containing more than two rings they must necessarily be branched. Specific examples of such straight chain alkylene groups are groups —$(CH_2)_n$— in which n is an integer from 6 to 12, for example 8, 9 or 10.

Alternative linking groups of especial interest are groups corresponding to a hydrocarbon group in which one or more carbon atoms are replaced by a nitrogen atom and/or in which one or more pairs of adjacent carbon atoms are replaced by a —CONH— group. Such groups are preferably of similar overall size (i.e. contain a similar total number of atoms in the backbone or chain thereof) to the hydrocarbon groups described above. Certain of such groups are of particular interest in the context of divalent linking groups for use in two ring compounds. These divalent groups may conveniently correspond to a straight chain alkylene group in which one carbon atom is replaced by a —NH— group and/or in which two pairs of adjacent carbon atoms are replaced by a —CONH— group. They will often contain one imino group in a substantially central position in the chain and/or one amido group located adjacent to each end of the chain, the carbonyl group thereof often being bonded to the terminal or penultimate carbon atom of the chain. Specific examples of such linking groups are

 (1)

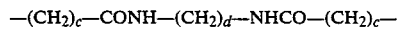 (2)

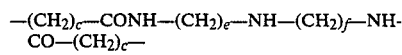 (3)

wherein a and b are each an integer from 2 to 6, for example 2 to 5, and especially a=2, b=3, or a=3, b=4, or a=5, b=5; c is an integer from 1 to 5, especially 1 to 3, for example 1 or 2, and d is an integer from 2 to 8, for example, c=1 and d=6, or c=2 and d=2 or 4; and e and f are each an integer from 2 to 4, for example c=1, e=2 and f=3, or c=2, e=2 and f=2 (values of d, e and f of 1 lead to linking groups containing the somewhat unstable

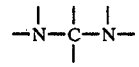

grouping). As regards the overall size of these linking groups, in the case of (2) it is preferred that $4 \leq 2c+d \leq 12$ and in the case of (3) it is preferred that $6 \leq 2c+e+f \leq 12$. In the case of the 1-hydroxypyrid-2-ones, where attachment of the linking group is likely to be to a carbon rather than a nitrogen atom, the linking groups used may often correspond to those described above but with an additional oxy group at each terminus thereof.

Trivalent linking groups of use in the present invention in the preparation of three ring compounds may include both the hydrocarbon and modified hydrocarbon types referred to hereinbefore. They are often similar to the divalent linking groups described above, modified so as to provide three groups terminating in a free valency arranged about the centre of the linking group instead of two. Groups of especial interest are a benzene group which is 1,3,5-substituted by three methylene groups and tripod groups consisting of a nitrogen atom substituted by three alkylene groups, for example straight chain groups of 1 to 6 carbon atoms and particularly 4 or 5 carbon atoms, or similar substituted benzene groups or tripod groups in which the methylene or alkylene groups are terminally substituted by a group —NHCO—$(CH_2)_c$— wherein c is as defined hereinbefore. In this latter case involving further terminal substitution, the three alkylene groups attached to the nitrogen atom of the tripod group may generally be somewhat shorter than previously indicated, preferably being straight chain and conveniently being of 1 to 4 carbon atoms, particularly of 2 or 3 carbon atoms when c is 1, for example of 2 carbon atoms each or of 2, 3 and 3 carbon atoms, respectively. Also of some considerable interest are trivalent groups similar to those divalent groups described above corresponding to an alkylene group in which one carbon atom is replaced by a —NH— group and also two pairs of carbon atoms are replaced by a —CONH— group. In this case, the trivalent group may be viewed as corresponding to a branched, trivalent hydrocarbon group in which a

group is replaced by

and three pairs of adjacent carbon atoms are replaced by a —CONH— group. Alternatively, they may be viewed in a closer analogy to the divalent groups as corresponding to a straight chain alkylene group in which a —CH$_2$— group is replaced by a

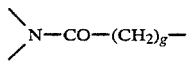

group wherein g is an integer from 1 to 3, especially being 1, and two pairs of carbon atoms are replaced by a —CONH— group. Again, these groups will often contain a nitrogen atom in a substantially central position in the chain and/or one amido group located adjacent to each end of the chain, the carbonyl group thereof often being bonded to the terminal or penultimate carbon atom of the chain. Specific examples of such linking groups are

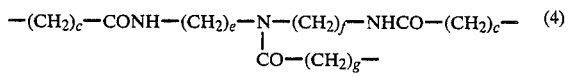 (4)

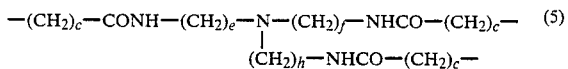 (5)

wherein c, e, f and g are as defined above and h is an integer from 1 to 4, and especially, for (4), c=1, e=2, f=3 and g=1, or c=1, e=3, f=4 and g=1, or c=1, e=3, f=4 and g=2, and for (5), c=1 and e=f=h=2 or c=2 and e=f=h=2. As regards the overall size of these linking groups, in the case of (4) it is preferred that 6≦2c+e+f≦12 whilst g is 1 to 3, and in the case of (5) it is preferred that for each of 2c+e+f, 2c+e+h and 2c+f+h the sum is greater than or equal to 6 but less than or equal to 12.

As regards tetravalent linking groups these may with particular convenience contain a fully branched carbon atom

which may be attached to four groups which are either wholly of a hydrocarbon nature or which additionally contain other groups such as those described hereinbefore. An example of this type of linking group has the form

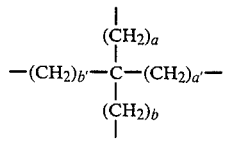

where each of a, a', b and b' is an integer from 1 to 6, for example the same integer, a particular linking group having each of a, a', b and b'=1.

By way of further guidance in the selection of suitable linking groups it may be stated that, for particularly preferred compounds, in the case of the 3-hydroxypyrid-2-ones the nitrogen atoms of the rings may conveniently be separated by 6 to 12, preferably 8 to 10 atoms, whilst with the 3-hydroxypyrid-4-ones a convenient range is 8 to 16, preferably 9 to 11 or 12 atoms. The situation with the 1-hydroxypyrid-2-ones will depend on the position of attachment of the linking groups but, in the preferred case of linking of the rings through the 4-position, the situation is analogous to that of the 3-hydroxypyrid-4-ones.

The compounds according to the present invention may be synthesised using various different approaches. In the case of the 3-hydroxypyridones, as mentioned hereinbefore, linkage is usually effected through the nitrogen atom of the ring. One approach, which is particularly applicable to the 3-hydroxypyrid-2-ones, involves reaction of the 3-hydroxypyridone, in a suitable proportion, with a reagent providing the linking group which contains the appropriate number of functional groups capable of reaction with the —NH— group of the pyridone. This procedure is of particular interest for the preparation of two ring compounds and suitable functional groups include the iodo group. Routes to C-substituted 3-hydroxypyridones are discussed in the UK patent application Nos. 8308056 and 8407181 and their equivalents referred to hereinbefore but, as indicated before, the more readily available compounds in which the carbon atoms of the ring are unsubstituted or substituted only by an aliphatic hydrocarbon group are of greater interest as starting materials.

A second approach involves reaction of a 3-hydroxypyridone which is N-substituted by a substituent containing a suitable first functional group with a reagent containing suitable second functional groups for reaction with said first group, the linking group deriving from both the N-substituent and the reagent. The procedure is of particular application for both the 3-hydroxypyrid-2- and -4 -ones in the preparation of two ring and three ring compounds, and suitable functional groups include a combination of a carboxy group and an amino group, either one of which may be attached to the 3-hydroxypyridone and the other of which to the reagent. Thus, the hydroxypyridone may, for example, be N-substituted by a group —(CH$_2$)$_i$—CO$_2$H or —(CH$_2$)$_i$—NH$_2$ wherein i is an integer from 1 to 5, for example 1, 2 or 3. The reagent in the former case, which is the preferred one, may be a di- or triamine, etc., and in the later case a di- or tri-carboxylic acid, although it will be appreciated that it is usual, whether the carboxy group is on the hydroxypyridone or the reagent, to activate it before reaction. Such activation may, for example, involve the use of an activated ester such as the p-nitrophenyl or 1-succinimyl ester and it will be usual to protect the ring hydroxy group, for example by benzylation, to prevent reaction thereof with the activated ester group or other form of activated carboxy group.

Yet a third approach may be used in the case of the 3-hydroxypyrid-4-ones where it is possible to react a di- or tri-amine, with a protected 3-hydroxy-4-pyrone, for example a 3-benzyloxy-4-pyrone, to replace the ring oxygen atom by a nitrogen atom of the reagent and thus effect linkage of two, three or more rings. Certain 3-hydroxy-4-pyrones, such as the unsubstituted compound and the 2-methyl substituted compound, maltol, are available commercially. Other readily available compound include the 6-methyl substituted compound, isomaltol, and other 2-alkyl substituted compounds whose synthesis is described in U.S. application Ser. No. 310,141 (series of 1960).

A specific example of such a first approach as described above involves the use of a reagent I—(CH$_2$)$_n$—I, wherein n is as defined hereinbefore, and the reagent $C(CH_2Br)_{4'}$; to prepare compounds containing two or four linked 3-hydroxypyrid-2-one or 3-hydroxypyrid-4-one rings, respectively, for example the rings (I) and (III) as shown hereinbefore. Specific examples of the second approach utilise a reagent $H_2N$—$(CH_2)_d$—$NH_2$, $H_2N$—$(CH_2)_e$—$NH$—$(CH_2)_f$—$NH_2$,

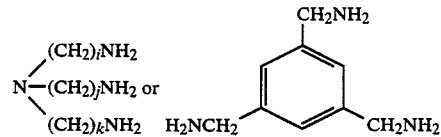

where d is as defined hereinbefore, for example being 2, 4, 6 or 8; e and f are as defined hereinbefore, for example being 2 and 3 respectively or each being 2; and i, j and k are each an integer from 1 to 4, for example each being 2 or being 2, 3 and 3 respectively. Such reagents are used to prepare compounds containing two or three linked rings by reaction with a 3-hydroxypyrid-2- or -4-one, for example one of the compounds (I) to (IV) as shown hereinbefore, which is N-substituted, for example by a group —$CH_2CO_2H$, —$(CH_2)_2$—$CO_2H$, —$(CH_2)_3$—$CO_2H$, —$(CH_2)_4$—$CO_2H$ or —$(CH_2)_5$—$CO_2H$ in activated form. The third approach may be used with a reagent similar to those described for use in the second approach, for example a reagent $H_2N$—$(CH_2)_a$—$NH$—$(CH_2)_b$—$NH_2$ where a and b are as defined hereinbefore, or $H_2N$—$(CH_2)_n$—$NH_2$ where n is as defined hereinbefore, for example being 8 or 9, or more conveniently with a reagent corresponding to a linking group (2), (3) or (4) as described above having c=1 and terminating at the free valencies in an amino group, such reagents being used to prepare compound containing two or three linked rings by reaction with 3-hydroxy-4-pyrones having a protected hydroxy group, for example the O-benzylated pyrones corresponding to the pyridones (II), (III) and (IV), followed by deprotection. (Such specific reagents may also be used in the second approach, although less conveniently, as an alternative to those described above.)

Consideration of these various approaches will show that, in some instances, certain of the linking groups described above are preferred in the case of certain types of hydroxypyridone and also that, in some instances, the same type of linking group may be produced by different approaches so that, for example, an amido function in the linking group may be present in the reagent used to form that group or may be produced by the reaction of an amine group and an activated ester group, one of which is attached to the reagent and the other to the hydroxypyridone ring. The selection of a synthetic route for the preparation of a particular compound will depend on various factors, including the relative availability of suitable intermediates.

It will be appreciated that the present invention extends to the various compounds, per se, obtainable by the specific examples of these three approaches described above for use in connection with the 3-hydroxypyridones.

In the case of the 1-hydroxypyrid-2-ones it is not possible to effect linkage of the rings through the nitrogen atoms thereof and linkage is therefore effected at one of the carbon atoms of the ring. The preferred approach to such linking is analogous to the second approach described above for the linking of 3-hydroxypyrid-2- and -4-ones in that it involves the use of a 1-hydroxypyrid-2-one having a substituent containing a suitable functional group, for example at the 4-position of the ring, which is reacted with a reagent containing suitable functional groups for reaction therewith. The previous discussion in relation to the second approach used with 3-hydroxypyrid-2- and -4-ones therefore applies also in the present case, with the modification that groups such as —$(CH_2)_i$—$CO_2H$ or —$(CH_2)_i$—$NH_2$, wherein i is as defined hereinbefore, are more usually attached to a ring carbon atom of a 1-hydroxypyrid-2-one through another group, particularly an —O— group, in view of the greater ease of synthesising aminoalkoxy and carboxyalkoxy substituted 1-hydroxypyrid-2-ones as compared with the aminoalkyl and carboxyalkyl substituted compounds. The synthesis of such substituted 1-hydroxypyrid-2-ones is discussed in detail in the co-pending applications of even date referred to hereinbefore but it may conveniently be achieved using a compound such as 2-chloro-4-nitropyridine-1-oxide for example, which may be subjected to nucleophilic substitution to replace the nitro group by a substituted alkoxy group which corresponds to or is convertible to that required, the chloro group then being converted to a hydroxy group by basic hydrolysis. It will be appreciated that the present invention extends to the various compounds, per se, obtainable using the specific reagents referred to above in connection with the second approach for the linking of 3-hydroxypyrid-2- and -4-ones when used in conjuction with a 1-hydroxypyrid-2-one which is C-substituted by a group —O—$(CH_2)_i$—$CO_2H$ or —O—$(CH_2)_i$—$NH_2$, wherein i is as defined hereinbefore and is preferably greater than 1 in the case of the latter type of group. The carboxy group will be in activated form in the former case, and both types of group may conveniently be substituted at the 4-position of the 1-hydroxypyrid-2-one.

Whilst it will usually be most convenient to use the compounds according to the present invention in the normal form, they may of course be used in salt form if desired, salts being formed between a physiologically acceptable cation and the anion formed by the loss of a proton from the ring hydroxy group. Moreover, appropriate substituent groups may of course be in salt form.

The synthesis of compounds according to the present invention and of various reagents providing linking groups between the hydroxypyridone rings is illustrated hereinafter in the Examples. Compound useful as reagents in the preparation of linking groups containing amide functions may readily be prepared from suitable amine precursors by reaction with the appropriate acylating agent, conveniently in the form of an activated ester. Thus, for example, the amine N-(2-aminoethyl)-1,3-propanediamine used in Example 6 may be reacted, as described in the footnote (1)(A) and (B) to that Example, with glycine in activated ester form and containing a protected amino group, for example as N-benzylglycine p-nitrophenyl ester, to provide, after removal of the N-protecting group, the compound $H_2N$—$CH_2CONH$—$(CH_2)_2$—$NH$—$(CH_2)_3$—$NHCOCH_2$—$NH_2$ or the compound $H_2N$—$CH_2CONH$—$(CH_2)_2$—$N(COCH_2$—$NH_2)$—$(CH_2)_3$—$NHCOCO_2$—$NH_2$, depending on the conditions used. Thus, in ethyl acetate and like solvents the former compound will precipitate from the reaction mixture and the latter compound is not formed even in the presence of a three, rather than two, molar proportion of the glycine derivative. However, in a more polar solvent, such as dimethylformamide, a three molar proportion will lead to the formation of the latter compound. The former compound may be used as such in the preparation of two ring compounds or, alternatively, may be reacted in a solvent such as dimethylformamide with another amino acid. Thus, reaction with a suitable β-alanine derivative, for example, will lead to the formation of the compound $H_2N—CH_2CONH—(CH_2)_2—N(COCH_2CH_2—NH_2)—(CH_2)_3—NHCOCH_2—NH_2$.

It will be appreciated that the procedures which have been described and illustrated herein with particular reference to the production of two ring and three ring compounds may be applied with appropriate modification for the production of compounds containing more rings than this. Moreover, it will be appreciated that the routes described are not the only routes available to the compounds of the present invention and that various alternatives may be used as will be apparent to those skilled in the art.

The compounds may be formulated for use as pharmaceuticals for veterinary, for example in an avian or especially a mammalian context, or particularly human use by a variety of methods. For instance, they may be applied as an aqueous, oily or emulsified composition incorporating a liquid diluent which most usually will be employed for parenteral administration and therefore will be sterile and pyrogen free. However, it will be appreciated from the foregoing discussion in relation to desferrioxamine that oral administration is to be preferred, and the compounds of the present invention may be given by such a route. Although compositions incorporating a liquid diluent may be used for oral administration, it is preferred to use compositions incorporating a solid carrier, for example a conventional solid carrier material such as starch, lactose, dextrin or magnesium stearate, the oral composition then conveniently being of a formed type, for example as tablets capsules, (including spansules), etc.

Other forms of administration than by injection or through the oral route may also be considered in both human and veterinary contexts, for example other forms known in the art such as the use of suppositories or pessaries, particularly for human administration.

Compositions may be formulated in unit dosage form, i.e. in the form of discrete portions each comprising a unit dose, or a multiple or sub-multiple of a unit dose. Whilst the dosage of active compound given will depend on various factors, including the particular compound which is employed in the composition, it may be stated by way of guidance that satisfactory control of the amount of iron present in the human body will often be achieved using a daily dosage of about 0.1 g to 5 g, particularly of about 0.5 g to 2 g, veterinary doses being on a similar g/kg body weight ratio. However, it will be appreciated that it may be appropriate under certain circumstances to give daily dosages either below or above these levels. Where desired, more than one compound according to the present invention may be administered in the pharmaceutical composition or, indeed, other active compounds may be included in the composition.

The 3-hydroxypyrid-2-ones, 3-hydroxypyrid-4-ones and 1-hydroxypyrid-2-ones all possess a high affinity for iron(III), as evidenced by log $K_{sol}$ values (log $K_{sol}$ is defined as being equal to log $\beta_{Fe(L)n} + 21 — [pK_{sp} + n \log a_{L(H+)} + m \log a_{L(Ca++)}]$ where log $\beta_{Fe(L)n}$ is the cumulative affinity constant of the ligand in question for iron(III), $pK_{sp}$ is the negative logarithm of the solubility product for $Fe(OH)_3$ and has a value of 39, n and m are the number of hydrogen and calcium ions, respectively, which are bound to the ligand, and $a_{L(H+)}$ and $a_L(Ca++)$ are the affinities of the ligand for hydrogen ions and calcium ions, respectively). In order to solubilise iron(III) hydroxide, log $K_{sol}$ must be greater than 0 and in order to remove iron from transferrin, log $K_{sol}$ should be in excess of 6.0. The log $K_{sol}$ values for the single ring compounds 3-hydroxy-1-methylpyrid-2-one and 1,2-dimethyl-3-hydroxypyrid-4-one, by way of example, are 10.0 and 9.5, respectively, thus comparing favourably with those of the bidentate hydroxamates at about 4.0, of catechols at about 8.0, of desferrioxamine at 6.0, and of diethylenetriamine penta-acetic acid (DTPA) at 2.0.

The compounds of the present invention have certain advantages, as compared with the single ring compounds of the earlier UK patent applications referred to hereinbefore, in binding with metals. In particular, they tend to have higher stability constants thereby removing the need to use additional substituent groups to increase stability. This enhanced stability is due to the chelate effect, so that the reaction of, for example, a three ring hexadentate compound with iron(III) will involve a greater increase in entropy than with the equivalent single ring bidentate compound, whereas the enthalpy increase will be similar in each case. The superiority of the hexadentate ligand is clearly demonstrated by the "dilution effect", the fraction of iron(III) bound to the hexadentate compound being relatively independent of dilution, whereas with the bidentate compound, the binding is strongly dependent on dilution. The hexadentate compounds of the present invention will thus generally be superior to the corresponding single ring bidentate compound for combination with free iron. However, the size of the hexadentate compounds in some cases may interfere with their ability to combine with bound iron in ferritin, and consequently some of the single ring bidentate compounds may be more effective at removing iron from ferritin than the corresponding hexadentate ligand. The compounds are however fully effective at removing iron from transferrin and as such removal is effected a transfer will occur in the body of iron bound as ferritin to iron bound as transferrin, thus allowing the removal of that iron by the compounds. Although the lower efficiency of the compounds of the present invention, as compared with such single ring compounds, at removing iron from ferritin therefore presents no real problem, it may be advantageous in some cases to use the compounds of the present invention in admixture with a single ring compound, which may contain the same form of ring as in the linked compound with the same type of carbon-substitution or lack thereof, the same form of ring differently substituted or a different type of ring system, suitable single ring compounds being those described in the aforementioned three earlier UK patent applications and their equivalents. Particularly of interest are mixtures of compounds according to the present invention containing three 3-hydroxypyrid-2- or -4-one rings and a single ring compound of the same type substituted on the nitrogen atom thereof and optionally on one or more ring carbon atoms by an aliphatic hydrocarbon group of 1 to 6 carbon atoms, such single ring compounds being those described in UK patent application GB No. 2118176A (U.S. application Ser. No. 478,493) and its equivalents. Such mixtures of three ring and single ring compounds will exhibit very efficient iron removal characteristics, probably on the basis of free iron being taken up mainly by the three ring compounds and bound iron mainly by the single ring compounds from which it may then be abstracted by the three ring compounds.

In addition to the use described hereinbefore for the treatment of general iron overload, the linked hydroxypyridone compounds described herein are also for interest for use in certain pathological conditions where there may be an excess of iron deposited at certain sites even though the patient does not exhibit a general iron overload, this being the case, for example, in certain arthritic and cancerous conditions. Indeed in some patients having such conditions, the patient may exhibit an overall anaemia and the metal-free linked hydroxypyridone compounds may then be used in conjunction with an iron complex which will correct the overall anaemia whilst the metal-free compound will act to remove iron from pathological to physiological sites. This iron complex may be of various types but of particular interest are the iron complexes, and especially the 3:1 neutral iron(III) complexes, of the single ring compounds described in the aforementioned three earlier UK patent applications and their equivalents. These compounds may contain the same form of ring as in the linked compound with the same type of carbon substitution or lack thereof, the same form of ring differently substituted, or a different type of ring system. The aliphatic hydrocarbon group-substituted 3-hydroxypyrid-2- and -4-one compounds referred to above are again of particular interest. Alternatively, the metal-free linked hydroxypyridones may be used in conjunction with and iron complex which is a complex of such a linked hydroxypyridone, which may be the same or different, such linked hydroxypyridone iron complexes and their use in this context being discussed in detail hereinafter.

Although the major use of the metal-free compounds of the present invention is in the removal of iron, they are also of potential interest for the removal of some other metals which may be present in the body in deleterious amounts. Indeed, the compounds of the present invention are perhaps of greater interest in this respect than the single ring compounds as the ability to incorporate differing numbers of rings into the compounds allows them to be tailored to be particularly applicable for use with different metals. Thus the three ring hexadentate compounds are particularly suited to the removal of trivalent cations such as iron(III) or aluminium(III) with which they form a neutral 1:1 complex. On the other hand, the two ring tetradentate compounds are particularly suited to the removal of divalent cations such as copper(II) and magnesium(II), and the four ring octadentate compounds are particularly suited to the removal of the tetravalent cations such as plutonium (IV) and other related transuranic metals. Alternatively, compounds containing multiples of these numbers of rings may be of interest for binding with more than one metal atom so that, for example, a six ring compound may be used to form a neutral complex by binding with two iron atoms in the ferric form.

The present invention thus includes the use of a compound as defined hereinbefore for use in medicine, for example for the removal from the body of toxic amounts of metals, including copper, aluminium and particularly iron. Moreover, the invention also includes a method for the treatment of a patient having toxic amounts of a metal, for example copper, aluminium and particularly iron, in the body which comprises administering to said patient an amount of compound as defined hereinbefore to effect a reduction of the levels of this metal in the patient's body.

Uses of the compounds of the present invention for combination with metals other than iron may extend to the treatment of body fluids outside the body or even to quite other contexts than the treatment of patients. One particular area of some interest involves the treatment of patients on haemodialysis who may show a dangerous build up of aluminium in the body. For the treatment of such patients the compounds of the present invention may conveniently be insolubilised by attachment to a support material and then contacted with the patient's blood to remove aluminium therefrom. Other uses of the compounds extending beyond the removal of metals from the body and involving particularly plutonium, for example its recovery from waste materials, or even iron, may similarly conveniently require insolubilisation of the compound by attachment to a support material.

The support material used may conveniently be one of various types of polymer described in the art for use in similar contexts, for example a carbohydrate material which may be of an agarose, dextran or other type, or a polystyrene or other material such as is used in ion-exchange resins. Various approaches known in the art may be used for effecting attachment of the compounds to such support materials but it is preferred to effect such attachment through the linking groups although it is possible to use another substituent group on the hydroxypyridone ring such as an acidic or basic group which forms an amide type of linkage through reaction with a complementary group on the support material. Convenient approaches involving attachment through the linking groups are direct conjugation using substituent carbodiimides or indirect methods using labile p-nitrophenol or N-hydroxysuccinimide esters. However a wide range of other procesures is generally available, for example using acid anhydrides and a variety of double reagents.

Just as iron overload can pose problems in some patients, iron deficiency anaemia can pose problems in others. As well as being of value as the metal-free compounds for the treatment of conditions involving iron overload, the linked hydroxypyridones described hereinbefore are of interest in the iron complex form for the treatment of iron deficiency anaemia.

An adequate supply of iron to the body is an essential requirement for tissue growth in both man and animals. Although there is normally an ample amount of iron in the diet, the level of absorption of iron from food is generally low so that the supply of iron to the body can easily become critical under a variety of conditions. Iron deficiency anaemia is commonly encountered in pregnancy and may also present a problem in the newly born, particularly in certain animal species such as the pig. Moreover, in certain pathological conditions there is a mal distribution of body iron leading to a state of chronic anaemia. This is seen in chronic diseases such as rheumatoid arthritis, certain haemolytic diseases and cancer.

Although a wide range of iron compounds is already marketed for the treatment of iron deficiency anaemia, the level of iron uptake by the body from these compounds is often quite low, necessitating the administration of relatively high dosage levels of the compound. The administration of high dose, poorly absorbed, iron complexes may cause siderosis of the gut wall and a variety of side effects such as nausea, vomiting, constipation and heavy malodorous stools. We have now found that the iron complexes of the linked hydroxypyridones described hereinbefore are of particular value in the treatment of such conditions.

Accordingly the present invention further comprises an iron complex of a compound in which two or more rings, being a 3-hydroxypyrid-2-one, 3-hydroxypyrid-4-one or 1-hydroxypyrid-2-one, are linked.

The comments made hereinbefore in relation to $K_{part}$ values for the metal-free compounds and their corresponding iron complexes in the case of preferred compounds apply equally to the selection of preferred metal-free compounds and of preferred iron complexes. The comments made hereinbefore with regard to preferences as to the nature and position of linking groups and other substituents thus apply equally in relation to the iron complexes.

The iron complexes present in the pharmaceutical compositions according to the present invention preferably contain iron in the ferric state. Although the use of complexes containing iron in the ferrous state may be considered, such complexes tend to be less stable and are thus of less interest. The iron complexes are preferably neutral, i.e. there being an internal balance of charges between the metal cation or cations and the ligand or ligands bound covalently thereto without the necessity for the presence of a non-covalently bound ion or ions, for example a chloride ion, to achieve balance. Moreover, the use of linked hydroxypyridones containing ionisable substituent groups (or linking groups) is of less interest and it is preferred that this internal balance of charges is achieved by complexing with an iron cation or cations a compound containing the appropriate number of hydroxypyridone rings to thereby provide, by the loss of a hydroxy proton from each ring, the number of anionic groups $O^-$ necessary to neutralise the charge on the cation or cations. Although such neutrality may be achieved, for example, in a complex containing a 3:2 molar proportion of an anion from a two ring compound:iron(III), preferred neutral complexes of this type are those formed between the anion derived from a compound containing three, or a multiple of three, hydroxypyridone rings and a ferric cation, or the same multiple of ferric cations, particularly those containing a trivalent anion derived from a three ring compound and a single ferric cation. It will be appreciated, however, that the invention does not exclude the use of complexes in which the charge on the anion derived from the linked hydroxypyridone compound and that on the ferric cation or cations do not fully neutralise each other, for example owing to the presence of an ionisable linking group, so that association with a further non-covalently bound physiologically acceptable ion or ions is necessary to achieve a balance of charges, although such complexes are generally of lesser interest.

The present invention thus particularly includes a neutral iron complex containing 1 molar proportion of iron(III) and 1 molar proportion of a compound in which three rings, being a 3-hydroxypyrid-2-one, 3-hydroxypyrid-4-one or 1-hydroxypyrid-2-one, are linked. The use of neutral iron complexes according to the present invention is discussed hereinafter with particular reference to such 1:1 complexes.

The iron complexes are conveniently prepared by the reaction of the linked hydroxypyridone compound and iron ions, the latter conveniently being derived from an iron salt, particularly a ferric halide and especially ferric chloride. The reaction is conveniently effected in a suitable mutual solvent and water may often be used for this purpose. If desired, however, an aqueous/organic solvent mixture may be used or an organic solvent, for example ethanol, methanol, chloroform and mixtures of these solvents together and/or with water where appropriate. In particular, methanol or especially ethanol may be used as the solvent where it is desired to effect the separation of at least a major part of a by-product such as sodium chloride by precipitation whilst the iron complex is retained in solution. Alternative procedures may, however, be used and will be apparent to those skilled in the art.

It will be appreciated that the nature of the iron complex obtained by the reaction of a linked hydroxypyridone compound and iron ions will depend both on the proportion of these two reactants and upon the pH of the reaction medium. Thus, for the preparation of a 1:1 ferric complex, for example, the linked three ring hydroxypyridone compound and the ferric salt are conveniently mixed in solution in a 1:1 molar proportion and the pH adjusted to a value in the range of 6 to 9, for example 7 or 8. Adjustment of the pH may conveniently be effected by the addition either of sodium carbonate or of a hydroxide base such as sodium or ammonium hydroxide, the use of a hydroxide base being of particular interest when preparing the iron complexes in batches of 20 g or more. When using a hydroxide base, the reaction may conveniently be carried out in a medium containing water as the solvent, for example in water or an ethanol:water mixture, and the pH adjusted by the addition of a 2 molar aqueous solution of the base. It will be appreciated that the presence of water in the reaction mixture will lead to the retention of a by-product in the iron complex on evaporation of the solvent (a chloride where the iron salt is ferric chloride). However, this can be removed, if desired, by procedures such as crystallisation from a suitable solvent system or sublimation in the particular case of ammonium chloride.

Reaction to form the iron complex is generally rapid and will usually have proceeded substantially to completion after 5 minutes at about 20° C., although a longer reaction time may be used if necessary. Following separation of any precipitated by-product, such as sodium chloride in the case of certain solvent systems, the reaction mixture may conveniently be evaporated on a rotary evaporator or freeze dried to yield the solid iron complex. This may, if desired, be crystallised from a suitable solvent, for example water, an alcohol such as ethanol, or a solvent mixture, including mixtures containing an ether. The present invention thus further includes a process for the preparation of an iron complex of a linked hydroxypyridone compound as defined herinbefore which comprises reacting said compound with iron ions and isolating the resultant complex.

Whilst for some uses it may be appropriate to prepare the iron complex in substantially pure form, i.e. substantially free from by-products of manufacture, in other cases, for example with a solid oral formulation as described hereinafter, the presence of by-products such as sodium chloride may be quite acceptable. In general, however, the neutral 1:1 [linked hydroxypyridone compound; iron(III)] complex is of particular interest in a form free from by-products which are complexes containing different proportions of hydroxypyridone and iron. As indicated hereinafter, it may be advantageous under some circumstances for the iron complex to be used in admixture with the metal-free linked hydroxypyridone compound and, if desired, such a mixture may be obtained directly by reacting a molar proportion of the compound and iron ions of greater than 1:1.

The iron complexes may be formulated as pharmaceuticals for veterinary, for example in an avian or particularly a mammalian context, or human use by a variety of methods and the invention includes a pharmaceutical composition comprising an iron complex as hereinbefore defined together with a physiologically acceptable diluent or carrier. The comments made hereinbefore with regard to the formulation of the metal-free compounds apply equally to the iron complexes, although in this instance compositions for parenteral administration are of greater interest particularly in the context of animal treatment. The problems of iron deficiency anaemia in newly born pigs arise primarily during the first three weeks or so of their life when a very rapid weight gain takes place. The iron complexes of the present invention may be used to treat piglets directly by a parenteral route, for example intramuscular, or oral, for example as a liquid preparation "injected into the mouth". However, an alternative approach is to enhance the iron content of the milk on which the piglets are feeding by treating the mother pig using oral or parenteral administration, for example an injectable slow release preparation (such an approach may also be an interest in a human context). When it is applicable to feed piglets on foodstuffs other than the milk of the mother pig, it may also be possible to effect the pharmaceutical administration of the iron complex in this other foodstuff.

As with the metal-free compounds, the dosage of the hydroxypyridone iron complex which is given will depend on various factors, including the particular compound which is employed in the composition. It may be stated by way of guidance, however, that maintenance of the amount of iron present in the human body at a satisfactory level will often be achieved using a daily dosage, in terms of the iron content of the compound, which lies in a range from about 0.1 to 100 mg and often in a range from 0.5 to 10 mg, for example 1 or 2 mg, veterinary doses being on a similar g/Kg body weight ratio. However, it will be appreciated that it may be appropriate under certain circumstances to give daily dosages either below or above these levels. In general, the aim should be to provide the amount of iron required by the patient without administering any undue excess and the properties of the pharmaceutical compositions according to the present invention are particularly suited to the achievement of this aim. Where desired, an iron complex of more than one linked hydroxypyridone compound as described above may be present in the pharmaceutical composition or indeed other active compounds may be included in the composition, for example compounds having the ability to facilitate the treatment of anaemia, such as folic acid. Another additional component which may be included in the composition, if desired, is a source of zinc. Iron compounds used in the treatment of iron deficiency anaemia can inhibit the mechanism of zinc uptake in the body and this can cause serious side effects in the foetus when treating anaemia in a pregnant female. It is believed, however, that the iron complexes of the present invention have a further advantage in that they either do not have this effect or exhibit the effect at a lower level than the compounds at present used in the treatment of anaemia. Accordingly, it may often be the case that the level of zinc providing compound added to the composition may not require to be high or, with preferred formulations of the iron complexes, may be dispensed with altogether.

It has never before been appreciated that iron complexes such as those described herein might be used in a pharmaceutical context. Accordingly the present invention includes an iron complex defined hereinbefore for use in medicine, particularly in the treatment of iron deficiency anaemia (in the broad sense of this term).

We have found that the iron complexes described herein are of value in the treatment of iron deficiency anaemia both in humans and also in a veterinary context, particularly for the treatment of various mammalian species and especially pigs. The complexes will partition into n-octanol indicating that they are able to permeate biological membranes, this property being confirmed in practice by tests of the ability of the $^{59}$Fe labelled iron complexes to permeate erythrocytes. The ability of the compounds in this respect will depend on the nature of the substituent(s) present therein and the reflection of this ability in the $K_{part}$ values of various compounds has been referred to hereinbefore. Once present in the bloodstream, the complexes will donate iron to transferrin, a position of equilibrium being set up between the complexes and transferrin. It is because of the existence of this equilibrium that the corresponding metal-free linked hydroxypyridone compound may equally be used in the treatment of iron overload, although certain of these compounds may be of particular value for use in the free state for iron removal and others may be of particular value for use as iron complexes for iron supply.

Certain aspects of their formulation may enhance the activity of the complexes in particular contexts. Thus, the neutral 1:1 ferric complexes are of particular value as being stable over a wide pH range from about 4 or 5 up to 10 and even at the pH values of less than 4 prevailing in the stomach free iron should not be liberated. Thus, it has been observed that, even at pH 0.5, the iron of such a 1:1 complex is still bound although even though not necessarily by all six of the original covalent bonds. Moreover, when the complex is cleared from the stomach and reaches the small intestine any internal dissociation of the bonds within the complex should be reversed under the alkaline conditions prevailing therein. Protection of the iron complexes from the acidic conditions of the stomach should not therefore be necessary from the point of view of preventing the liberation of iron from the complex. It is a possible with some forms of linking group, however, that breakdown of the group may occur under the acidic conditions prevailing in the stomach, for example by cleavage of an amide group. In such circumstances, the use of a method of formulation which avoids or reduces exposure of the iron complex to the acidic conditions of the stomach can be of value. Such an approach may involve various types of controlled release system, ranging from one, which may for example be based on a polymer, which simply provides a delayed release of the complex with time, through a system which is resistant to dissociation under acidic conditions, for example by the use of buffering, to a system which and is biased towards release under conditions such as prevail in the small intestine, for example a pH sensitive system which is stabilised towards a pH of 1 to 3 such as prevails in the stomach but not one of 7 to 9 such as prevails in the small intestine. Since the pH of the stomach is higher after a meal, it may be advantageous, whatever method of formulation is used, to administer the iron complexes at such a time.

A particularly convenient approach to a controlled release composition involves encapsulating the iron complex by a material which is resistant to dissociation in the stomach but which is adapted towards dissociation in the small intestine (or possibly, if the dissociation is slow, in the large intestine). Such encapsulation may be achieved with liposomes, phospholipids generally being resistant to dissociation under acidic conditions. The liposomally entrapped 1:1 iron(III) complexes can therefore survive the acid environment of the stomach without dissociation. On entry into the small intestine, the pancreatic enzymes rapidly destroy the phospholipid-dependent structure of the liposomes thereby releasing the 1:1 complex. Liposome disruption is further facilitated by the presence of bile salts. However, it is usually more convenient to effect the encapsulation, including microencapsulation, by the use of a solid composition of a pH sensitive nature.

The preparation of solid compositions adapted to resist dissociation under acidic conditions but adapted towards dissociation under non-acidic conditions is well known in the art and most often involves the use of enteric coating, whereby tablets, capsules, etc., or the individual particles or granules contained therein, are coated with a suitable material. Such procedures are described, for example, in the article entitled "Production of enteric coated capsules" by Jones in Manufacturing Chemist and Aerosol News, May 1970, and in such standard reference books as "Pharmaceutical Dosage Forms, Volume III by Liebermann and Lackmann (published by Marcel Decker). One particular method of encapsulation involves the use of gelatine capsules coated with a cellulose acetate phthalate/diethylphthalate layer. This coating protects the gelatin capsule from the action of water under the acid conditions of the stomach where the coating is protonated and therefore stable. The coating is however destabilised under the neutral/alkaline conditions of the intestine where it is not protonated, thereby allowing water to act on the gelatin. Once released in the intestine the rate of permeation of the intestine wall by the water soluble 1:1 iron-(III) complex is relatively constant irrespective of the position within the intestine, i.e. whether in the jejunum, ileum or large intestine. Other examples of methods of formulation which may be used include the use of polymeric hydrogel formulations which do not actually encapsulate the iron complex but which are resistant to dissociation under acidic conditions.

Another aspect of the formulation of the iron complexes to confer certain particular advantages is the use of a metal-free linked hydroxypyridone compound in admixture with its iron complex. Thus, as mentioned hereinbefore, in certain pathological conditions there may be an excess of iron deposited at certain sites even though the patient exhibits an overall anaemia. In patients having such conditions the use of such a mixture has the advantage that the iron complex will remedy the overall anaemia whilst the free linked hydroxypyridone compound will act to remove iron from pathological to physiological sites. Moreover, there may be an advantage in formulating the iron complex of one compound as described herein with another one of such compounds in the metal-free form. Thus, it is preferable for the linked hydroxypyridone compound present in an iron donor to be rapidly metabolized so as to effect its removal from the system once it has given up its iron at an appropriate site in the system, whilst it is preferable for a linked hydroxypyridone compound being used as an iron remover not to be rapidly metabolized so that it remains in the system, taking up iron, for an extended period. For this reason the use of different linked hydroxypyridone compounds in the free form and as the iron complex has certain advantages. Moreover, different compounds may, for other reasons, function more efficiently either in the free form as an iron remover or in complex form as an iron donor. If desired, the free compound may alternatively be used in the form of a salt formed with the anion produced by the loss of a hydroxy proton and containing a physiologically acceptable cation, for example as described hereinbefore. As an alternative to combination with a different metal-free linked hydroxypyridone compound of the same type, the iron complex may be used in combination with another iron chelating agent.

When using such a mixture of an iron complex of a linked hydroxypyridone compound and a metal-free compound, the daily dosage of the iron complex may be as previously described and the daily dosage of the free compound may also be that described in relation to the use of such compounds in iron overload conditions.

It will be appreciated that the present invention also includes a method for the treatment of a patient which comprises administering to said patient an amount of an iron complex as described hereinbefore in order to effect an increase in the levels of iron in the patient's blood stream.

In addition to the pharmaceutical uses of the iron complexes discussed above they are also of potential interest as a source of iron in various other contexts including in cell and bacterial growth, in plant growth, as a colouring agent and in the control of iron transport across membranes.

The invention is illustrated by the following Examples which described the preparation of various compounds of the form

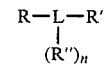

wherein R, R" and R" each represent a substituted or unsubstituted 3-hydroxypyrid-2-one, 3-hydroxypyrid-4-one or 1-hydroxypyrid-2-one ring, n represents 0 or an integer 1, 2, 3, 4 etc. (no rings R" being present when n is 0) and L represents a linking group.

The exemplified compounds contain two or three 3-hydroxypyrid-2-one or 3-hydroxy-2-methylpyrid-4-one rings joined by a variety of linking groups. For greater ease of reference the different compounds described in the Examples are illustrated in Table 1, the numbering of the compounds corresponding to that of the Examples. It will be appreciated that further compounds may be produced by using in the procedures of Examples 2, 3, 7 and 9 the corresponding 3-hydroxypyrid-2-one reagent with the same linking group reagents as described in these Examples and in the procedures of Examples 4, 5, 8 and 10 the corresponding 3-hydroxy-2-methylpyrid-4-one reagent with the same linking reagents as described in these Examples. Such further specific compounds comprising 3-hydroxypyrid-2-one rings with a linking group such as is present in compounds 2, 3, 7 and 9 and 3-hydroxy-2-methylpyrid-4-one rings with a linking group such as is present in compounds 4, 5, 8 and 10 are thus also individually included within the scope of the present invention.

It will also be noted that, as discussed hereinbefore in relation to the preparation of amine reactants, a change in the nature of the solvent used can produce a different reaction product. Thus, in Example 7 where methylene chloride is used, the secondary amine group in the reactant does not react with the active ester, while in Example 8 where the more poler dimethylformamide is used as the solvent, the secondary amine group in the reactant does react with the active ester. It will be appreciated therefore that different products containing three rather than two rings, or vice versa, may be obtained in the procedures of Examples 7, 8, 9 and 10 by using different reaction conditions and that these alternative compounds are also individually included within the scope of the present invention.

TABLE 1

| Compound | Number of rings | Ring system | Linking group |
| --- | --- | --- | --- |
| 1 | 2 | 3-hydroxy-2-methyl-4-pyridinone | $-CH_2-(CH_2)_6-CH_2-$ |
| 1A | 2 | 3-hydroxy-2-methyl-4-pyridinone | $-CH_2-(CH_2)_7-CH_2-$ |
| 2 | 2 | 3-hydroxy-2-methyl-4-pyridinone | $-(CH_2)_2-CONH-(CH_2)_8-NHCO(CH_2)_2-$ |
| 3 | 2 | 3-hydroxy-2-methyl-4-pyridinone | $-(CH_2)_5-CONH-(CH_2)_2-NHCO(CH_2)_5-$ |
| 3A | 2 | 3-hydroxy-2-methyl-4-pyridinone | $-(CH_2)_3CONH-(CH_2)_2-NHCO(CH_2)_3-$ |
| 3B | 2 | 3-hydroxy-2-methyl-4-pyridinone | $-CH_2CONH-(CH_2)_2-NHCOCH_2-$ |
| 4 | 2 | 3-hydroxy-2-pyridinone | $-CH_2CONH-(CH_2)_6-NHCOCH_2-$ |

TABLE 1-continued

| Compound | Number of rings | Ring system | Linking group |
|---|---|---|---|
| 5 | 2 | 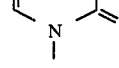 | —CH$_2$CONH—(CH$_2$)$_8$—NHCOCH$_2$— |
| 6 | 2 | 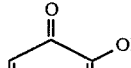 | —(CH$_2$)$_3$—NH—(CH$_2$)$_2$— |
| 6A | 2 | 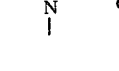 | —CH$_2$CONH—(CH$_2$)$_2$—NH—(CH$_2$)$_3$—NHCOCH$_2$— |
| 6B | 3 | 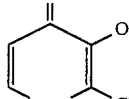 | —CH$_2$CONH—(CH$_2$)$_2$—N—(CH$_2$)$_3$—NHCOCH$_2$—<br>                                       COCH$_2$— |
| 6C | 3 |  | —CH$_2$CONH—(CH$_2$)$_3$—N—(CH$_2$)$_4$—NHCOCH$_2$—<br>                                       COCH$_2$— |
| 7 | 2 | 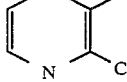 | —(CH$_2$)$_2$CONH—(CH$_2$)$_4$—NH—(CH$_2$)$_3$—NHCO(CH$_2$)$_2$— |
| 8 | 3 | 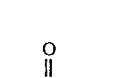 | —CH$_2$CONH—(CH$_2$)$_2$—N—(CH$_2$)$_2$—NHCOCH$_2$—<br>                           (CH$_2$)$_2$—NHCOCH$_2$— |
| 9 | 3 | 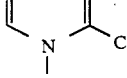 | —(CH$_2$)$_2$CONH—(CH$_2$)$_2$—N—(CH$_2$)$_2$—NHCO(CH$_2$)$_2$—<br>                             (CH$_2$)$_2$—NHCO(CH$_2$)$_2$— |

TABLE 1-continued

| Compound | Number of rings | Ring system | Linking group |
|---|---|---|---|
| 10 | 3 | 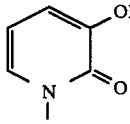 | —CH₂CONH—(CH₂)₃—N—(CH₂)₃—NHCOCH₂—<br>                                    |<br>                               COCH₂— |

EXAMPLES

Example 1

Preparation of
1,8-di-(3-hydroxy-2-methyl-4-oxopyrid-1-yl)octane and other related compounds 3-Hydroxy-2-methyl-4-pyrone (22.2 g) in methanol (225 ml) is added to aqueous sodium hydroxide (25 ml H₂O containing 7.5 g NaOH). Benzyl chloride (25.5 g) is added and the mixture is refluxed for 6 hours and is then allowed to cool overnight. The bulk of the methanol is removed under vacuum and the residue is treated with water (50 ml). The mixture is extracted into dichloromethane (3×25 ml). The extracts are combined, washed with 5% w/v NaOH (2×25 ml), then water (2×25 ml) and dried over magnesium sulphate. Evaporation of the solvent gives crude 3-benzyloxy-2-methyl-4-pyrone or "benzyl maltol" (35 g, 92%) which is purified by distillation in nitrogen under reduced pressure to yield a colourless oil (28 g) of b.p. 148° C./0.2 mm.

3-Benzyloxy-2-methyl-4-pyrone (0.066 moles) and 1,8-diaminooctane (0.022 moles) are mixed in 2:1 v/v aqueous methanol (300 ml), solid sodium hydroxide (2 g) is added, and the mixture is heated on a steam bath for 5 hours. The mixture is allowed to cool and an aliquot is taken, acidified to pH 2 with concentrated hydrochloric acid and the solvent removed on the rotary evaporator to give a solid residue. This residue is checked for completion of the reaction through its n.m.r. spectrum, the presence of protons exchangeable at ca δ=8.3 (d₆DMSO) showing that the reaction is not complete. If this is the case, refluxing is continued until the solid obtained from an aliquot shows no such protons. On complete reaction being found to have occurred, the mixture is cooled and acidified to pH 2 with concentrated hydrochloric acid, any precipitate formed at this stage being dissolved by the addition of methanol to the mixture. Palladium/carbon catalyst is then added and the solution is hydrogenated at room temperature and atmospheric pressure in order to effect debenzylation. The catalyst is removed by filtration and the solvent by rotary evaporation, the resulting solid then being recrystallised from water to give the title compound[1] in 40% yield as a white solid of m.p. 297°–300° dec; $\gamma_{max}$ (nujol) 1340 and 1620 cm⁻¹; δ(d₆DMSO/D₂O), 1.5 (m, 12H), 2.5 (s, 6H), 4.3 (m, 4H), 7.1 (d, 2H) and 8.1 (d, 2H); m/e 360.

[1] In a variation of the above procedure, 3-benzyloxy-2-methyl-4-pyrone is reacted with 1,9-diaminononane to give compound 1A, 1,9-di-(3-hydroxy-2-methyl-4-oxopyrid-1-yl)-nonane in 45% yield as a white solid of m.p. 275°–280° C. dec; $\gamma_{max}$ (nujol) 1420 and 1620 cm⁻¹; δ(d₆DMSO), 1.2–2.1 (m, 14H), 2.7 (s, 6H), 4.4 (m, 4H), 7.3 (d, 2H) and 8.3 (d, 2H); m/e 374.

Example 2

Preparation of
1,8-di-[3-(3-hydroxy-2-methyl-4-oxopyrid-1-yl)propionamido]-octane β-Alanine (5 g) in water (50 ml) is added to 3-benzyloxy-2-methyl-4-pyrone (10 g) in 95% ethanol (100 ml) and sodium hydroxide (4 g) in water (50 ml) is then slowly added to the reaction mixture until a pH of 13 is obtained. The solution is refluxed for 15 minutes during which time the colour changes from yellow to amber. After cooling, the solution is acidified to pH 2.5 with concentrated HCl (about 2 ml) and is then rotary evaporated at 50° C. The resulting oil is subjected to a methylene chloride/water extraction. The solid which remains is triturated with acetone and recrystallised from water to give 3-benzyloxy-1-(2'-carboxyethyl)-2-methylpyrid-4-one, m.p. 81°–83° C.

The 3-benzyloxy-1-(2'-carboxyethyl)-2-methylpyrid-4-one (1 g) and N-hydroxysuccinamide (0.45 g) are dissolved in methylene chloride (7 ml) and dicyclohexyl carbodiimide (0.8 g) in methylene chloride (3 ml) is added slowly at 0° C. with stirring. After 15 minutes the precipitate which has formed is separated by filtration and the filtrate is added to a solution of 1,8-diaminooctane (0.2 g) in methylene chloride (5 ml). The reaction mixture is then rotary evaporated to yield an oil which is dissolved in ethanol (30 ml) and hydrogenated over a palladium/charcoal catalyst. Evaporation of the solution remaining after separation of the catalyst yields an oil which is dissolved in acetone, the solution then being treated with HCl gas. The resultant dihydrochloride salt which is precipitated from solution is triturated with diethyl ether to give a low melting solid. This solid is further purified by chromatography on Sephadex G-IO to yield the title compound as the dihydrochloride salt in approximately 50% yield, δ(d₆DMSO) 1.1 (m, 8H), 1.9 (m, 4H), 2.5 (s, 6H), 2.7 (m, 4H), 2.9 (m, 4H), 4.5 (t, 4H), 7.3 (d, 2H), 8.1 (d, 2H).

Example 3

Preparation of
1,2-di-[6-(3-hydroxy-2-methyl-4-oxopyrid-1-yl)hexanamido]-ethane and other related compounds 6-Aminocaproic acid is reacted with 3-benzyloxy-2-methyl-4-pyrone in an exactly analogous procedure to that described in Example 2 for the reaction of the latter compound with β-alanine to give 3-benzyloxy-1-(5'-carboxypentyl)-2-methylpyrid-4-one in 70% yield, this compound being obtained after recrystallisation from ethanol/acetone (1:1 v/v) as white crystals, m.p. 145°–147° C.

3-Benzyloxy-1-(5'-carboxypentyl)-2-methylpyrid-4-one (1 g) and N-hydroxysuccinimide (0.4 g) are dissolved in methylene chloride (20 ml) and dicyclohexylcarbodiimide (0.7 g) in methylene chloride (5 ml) is added slowly at 0° C. with stirring. After 20 minutes the resulting precipitate is separated by filtration and the filtrate is treated with stirring with a solution of diaminoethane (0.092 g) in methylene chloride (1 ml). A flocculant precipitate is formed which is filtered to give a very hygroscopic solid which rapidly forms an oil. This oil is dissolved in 95% ethanol and hydrogenated over a platinum/charcoal catalyst. The solution remaining after separation of the catalyst is rotary evaporated to yield an oil which is triturated with acetone and then with diethyl ether to yield the title compound as a hygroscopic buff solid, $\delta(d_6DMSO)$ 1.0-1.7 (m, 12H), 2.0 (s, 6H), 2.2 (m, 4H), 3.0 (m, 4H), 3.8 (m, 4H), 6.0 (d, 2H), 7.4 (d, 2H), 7.7 (m, 2H). (1) In a variation of this procedure the compounds 3-benzyloxy-1-(3'-carboxypropyl)-2-methylpyrid-4-one and 3-benzyloxy-1-carboxymethyl-2-methylpyrid-4-one are prepared in an analogous manner using 4-aminobutyric acid and glycine, respectively, then converted to the active ester and reacted with diaminoethane to give (A) 1,2-di-[4-(3-hydroxy-2-methyl-4-oxopyrid-1-yl)-butanamido]-ethane and (B) 1,2-di-(3-hydroxy-2-methyl-4-oxopyrid-1-ylacetamido)-ethane, respectively.

Example 4

Preparation of 1,6-di-(3-hydroxy-2-oxopyrid-1-ylacetamido)-hexane 2,3-Dihydroxypyridine (10 g) is suspended in ethylbromoacetate (40 ml) and the mixture is heated in a sealed tube for 24 hours at 140° C. The tube is then cooled in solid $CO_2$ and opened. The contents are subjected to rotary evaporation at 50° C. to yield a yellow solid. Recrystallisation of this solid from water yields 1-ethoxycarbonylmethyl-3-hydroxypyrid-2-one as white crystals (10.8 g), m.p. 141°-151° C.

1-Ethoxycarbonylmethyl-3-hydroxypyrid-2-one (10 g) is dissolved in methanol/water (9:1 v/v) (400 ml). To this solution is added benzyl chloride (3 molar excess) and NaOH until the pH is above 12. The mixture is then refluxed for six hours to give a clear orange solution. The methanol is removed by rotary evaporation and the aqueous solution is extracted with dichloromethane to remove excess benzyl chloride. The aqueous phase is diluted slightly by adding extra water and then acidified to pH 2 using concentrated hydrochloric acid which results in the precipitation of a beige solid. The mixture is cooled and the precipitate filtered off and washed with diethyl ether. The crude product is recrystallised from ethanol to give 3-benzyloxy-1-carboxymethyl-pyrid2-one (5.4 g, 41%), m.p. 176°-177° C.

3-Benzyloxy-1-carboxymethylpyrid-2-one (0.5 g) and N-hydroxysuccinimide (0.25 g) are dissolved in dimethylformamide (10 ml) and the solution cooled in an ice bath. Dicyclohexylcarbodiimide (0.45 g) dissolved in dimethylformamide (10 ml), is added to the pyridone and allowed to stand for 18 hours. The precipitated dicyclohexylurea is separated by filtration and the filtrate evaporated to dryness. The resultant residue is recrystallised from a methylene chloride/diethylether mixture to yield 3-benzyloxy-1-succinimyloxycarbonyl-methylpyrid-2-one (0.56 g, 80%), m.p. 183°-184° C.

3-Benzyloxy-1-succinimyloxycarbonylmethylpyrid-2-one (0.5 g) is dissolved in dimethylformamide (12.5 ml). To this solution is added a solution of 1,6-diaminohexane (0.5 molar equivalent) in methanol (5 ml). The resulting white precipitate is separated by filtration and the colourless filtrate is evaporated to dryness. The resultant residue is extracted with a chloroform/water mixture, the organic layer being dried ($Na_2SO_4$) and evaporated to dryness. The resultant residue is dissolved in ethanol containing 1% v/v of acetic acid and hydrogenated over palladium charcoal. Filtration, evaporation and recrystallisation from ethanol yields the title compound as a white crystalline solid in 70% yield, m.p. 240°-242° C.; $\nu_{max}$(nujol) 1645, 1580, 1555 cm$^1$; $\delta(d_6DMSO)$ 1.2 (s, 8H), 2.9 (s, 4H), 4.15 (s, 4H), 5.9 (t, 2H), 6.5 (d, 2H), 6.8 (d, 2H), 7.9 (t, 2H), 8.7 (s, 2H).

Example 5

Preparation of 1,8-di-(3-hydroxy-2-oxopyrid-1-yl)-acetamido)-octane

3-Benzyloxy-1-succinimyloxycarbonylmethylpyrid-2-one—prepared as described in Example 4—is reacted with 1,8-diamino-octane in an analogous manner to that described for the reaction of this compound with 1,6-diaminohexane in Example 4 to yield the title compound in 76% yield, m.p. 238°-239° C.; $\nu_{max}$ (nujol) 1650, 1580, 1560 cm$^{-1}$; $\delta(d_6DMSO)$ 1.2 (s, 12H), 4.4 (s, 4H), 5.9 (t, 2H), 6.6 (d, 2H), 6.9 (d, 2H), 8.0 (t, 2H), 8.8 (s, 2H).

Example 6

Preparation of N-[2-(3-hydroxy-2-methyl-4-oxopyrid-1-yl)-ethyl]-3[3-(3-hydroxy-2-methyl-4-oxopyrid-1-yl)-propylamine and other related compounds 3-Benzyloxy-2-methyl-4-pyrone (5.2 g, crude) is dissolved in a mixture of ethanol (100 ml) and water (200 ml) containing sodium hydroxide (2 g), the pH of the resulting solution being about 12 to 13. The tri-amine, N-(2-aminoethyl)-1,3-propanediamine (0.75 g), is then added to give a reaction mixture which contains a 3.75 molar excess of the 4-pyrone to tri-amine. The mixture is stirred at room temperature for 6 days and is then acidified with concentrated HCl to pH 2 and rotary evaporated to give a brown solid. This solid is extracted with ethanol from which a white solid is obtained on rotary evaporation. Recrystallisation from water gives N-[2-(3-hydroxy-2-methyl-4-oxopyrid-1-yl]-3-(3-hydroxy-2-methyl-4-oxopyrid-1-yl-propylamine (1.5 g). This product is hydrolysed by refluxing in 40% w/w/ HBr in $CH_3CO_2H$ (ca 300 ml) on a steam bath for 30 minutes. The acids are removed by rotary evaporation (<1 mm Hg) and water is added to the resulting oil to give a white precipitate. This precipitate is redissolved by heating and recrystallised by cooling to give the title compound[(1)] (0.66 g, 31%) as large elongated off-white crystals of m.p. 137°-140° C.; $\gamma_{max}$ (nujol) 804, 1020, 1500, 1540, 1630 and 3400 cm$^{-1}$; $\delta(d_6DMSO)$ 2.2 (m, 2H), 2.5 (s, 3H), 3.1 (m, 2H), 3.5 (m, 2H), 4.4-4.8 (m, 4H), 7.2 (d, 1H)) and 8.4 (d, 1H). (1) In a variation of this procedure the following alternative amines are prepared.

(A)

N-[2-(Aminoacetamido)-ethyl]-3-(aminoacetamido)-propylamine

The p-nitrophenyl ester of N-benzylglycine (2 g) and N-(2-aminoethyl)-1,3-propanediamine (0.18 g) are dissolved in ethylacetate (30 ml). After standing for 1 hour, the mixture is filtered, evaporated and resulting solid triturated with diethyl ether. Recrystallisation of the product from ethanol yields N-[2-(benzylaminoacetamido)-ethyl]-3-(benzylaminoacetamido)-propylamine as a solid, $\nu_{max}$ (nujol) 1680, 1630, 1540 cm$^{-1}$; $\delta$(d$_6$DMSO) 1.5 (quintet, 2H), 2.5 (m, 4H), 3.1 (q, 4H), 3.6 (d, 4H), 5.0 (s, 4H), 7.3 (s, 10H), 7.4 (m, 2H), 7.7 (m, 2H).

Hydrogenation of this compound in ethanol containing 1% v/v of acetic acid over palladium/charcoal gives a 75% yield of the title compound as a viscous oil.

(B)
N-(Aminoacetamido)-N-[2-(aminoacetamido)-ethyl]-3-(aminoacetamido)-propylamine The p-nitrophenyl ester of N-benzylglycine and N-(2-aminoethyl)-1,3-propane diamine are reacted in the same proportions as in (A) above but in dimethyl formamide as the solvent to yield, after working up in a similar manner, N-(N-benzylglycyl)-N-[2-(benzylaminoacetamido)-ethyl]-3-(benzylaminoacetamido)-propylamine in 65% yield, $\delta$(d$_6$DMSO) 1.6 (m, 2H), 3.2 (m, 6H), 3.5 (d, 4H), 3.8 (d, 2H), 5.0 (s, 6H), 7.3 (s, 15H), 7.4 (m, 3H), 7.8 (m, 3H). Hydrogenation as in (A) above yields the title compound in 75% yield as an oil.

(C)
N-(Aminoacetamido)-N-[3-(aminoacetamido)-propyl]-4-(aminoacetamido)-butylamine The p-nitrophenyl ester of N-benzylglycine and N-(3-aminopropyl)-1,4-butane diamine are reacted together and the reaction mixture worked up in a similar manner to that described in (B) above for the reaction of this ester with N-(2-aminoethyl)-1,3-propanediamine to give N-(N-benzylglycyl)-N-[3-(benzylaminoacetamido)-propyl]-4-(benzylaminoacetamido)-butylamine, $\nu_{max}$ (nujol) 1660, 1625 cm$^{-1}$; $\delta$(d$_6$DMSO) 1.4 (m, 6H), 3.1 (m, 6H), 3.2 (s, 4H), 3.5 (d, 4H), 3.8 (d, 2H), 5.0 (s, 6H), 7.3 (s, 15H), 7.4 (m, 3H), 7.8 (m, 3H). Hydrogenation as in (A) above yields the title compound in 70% yield as an oil.

The three amines prepared as described under (A), (B) and (C) are reacted with 3-benzyloxy-2-methyl-4-pyrone in an analogous manner to that described in this Example for N-(2-aminoethyl)-1,3-propanediamine to give, respectively, N-[2-(3-hydroxy-2-methyl-4-oxopyrid-1-ylacetamido)-ethyl]-3-(3-hydroxy-2-methyl-4-oxopyrid-1-ylacetamido)-propylamine, N-(3-hydroxy-2-methyl-4-oxopyrid-1-ylacetyl)-N-[2-(3-hydroxy-2-methyl-4-oxopyrid-1-ylacetamido)-ethyl]-3-(3-hydroxy-2-methyl-4-oxopyrid-1-ylacetamido)-propylamine and N-(3-hydroxy-2-methyl-4-oxopyrid-1-ylacetyl)-N-[3-(3-hydroxy-2-methyl-4-oxopyrid-1-ylacetamido)-propyl]-4-(3-hydroxy-2-methyl-4-oxopyrid-1-ylacetamido)-butylamine.

Example 7

Preparation of
N-[3-(3-hydroxy-2-methyl-4-oxopyrid-1-ylpropionamido)-propyl]-4-(3-hydroxy-2-methyl-4-oxopyrid-1-ylpropionamido)-butylamine 3-Benzyloxy-1-(2'succinimyloxycarbonylethyl)-2-methylpyrid-4-one is prepared from 3-benzyloxy-1-carboxyethylpyrid-2-one by reaction with N-hydroxysuccinimide as described in Example 1, the compound being isolated in an analogous manner to that described in Example 4 for the corresponding 1-(2'succinimyloxycarbonylethyl) compound. The compound is obtained in 60% yield as a solid of m.p. 144°–146° C.; $\nu_{max}$ (nujol) 1800, 1770, 1735, 1625, 1570 cm$^{-1}$; $\delta$(CDCl$_3$) 2.0 (s, 3H), 2.8 (s, 4H), 2.9 (t, 2H), 4.1 (t, 2H), 5.1 (s, 2H), 6.3 (d, 1H), 7.3 (s, 5H), 7.3 (d, 1H).

3-Benzyloxy-1-(2'succinimyloxycarbonylethyl)-2-methylpyrid-4-one (0.5 g) is dissolved in methylene chloride (30 ml) and the solution is added dropwise over 15 minutes to spermidine [N-(3-aminopropyl-butylamine) (0.19 g) in methylene chloride (10 ml). The resulting solution, is allowed to stand for 1 hour and is then washed with water, dried (Na$_2$SO$_4$) and evaporated to give N-[3-(3-benzyloxy-2-methyl-4-oxopyrid-1-ylacetamido)-propyl]-4-(3-benzyloxy-2-methyl-4-oxopyrid-1-ylacetamido)-butylamine in 70% yield as an oil, which on trituration with cold ethanol followed by recrystallisation from ethanol gives a white solid, m.p. 89° C.; $\nu_{max}$ (nujol) 3250, 1640 1590 cm$^{-1}$; $\delta$(d$_6$DMSO) 1.4 (m, 6H), 2.4 (s, 6H), 2.6 (m, 4H), 2.8 (m, 4H), 4.4 (t, 4H), 4.9 (s, 4H), 7.3 (s, 10H), 8.1 (m, 2H), 8.6 (d, 2H). Hydrogenation of this dibenzyl derivative over palladium/charcoal in ethanol containing 1% v/v acetic acid in an analogous fashion to that described in Example 4 yields the title compound as an oil.

Example 8

Preparation of
N,N-di-[2-(3-hydroxy-2-oxopyrid-1-ylacetamido)-ethyl]-2-(3-hydroxy-2-oxopyrid-1-ylacetamido)-ethylamine 3-Benzyloxy-1-succinimyloxycarbonylmethylpyrid-2-one—prepared as described in Example 4—(2.1 g) is dissolved in dimethylformamide (50 ml) and tri-(2'-aminoethyl)-amine (0.3 g) is added with stirring. The resultant solution is stirred for 10 minutes and is then evaporated to dryness. The residue is extracted with methylene chloride/water, the organic layer being evaporated to dryness. The residue is dissolved in 95% ethanol and hydrogenated over palladium/charcoal, filtration and evaporation yielding a solid which is desiccated over solid NaOH. Recrystallisation of the desiccated solid from 95% ethanol yields the title compound (0.82 g, 68%) as a white solid, m.p. 112°–114° C.; $\nu_{max}$ (nujol) 1650, 1590 cm$^{-1}$; $\delta$(d$_6$DMSO) 2.3 (s, 6H), 2.95 (s, 6H), 4.4 (s, 6H), 5.9 (t, 3H), 6.55 (d, 3H), 6.9 (d, 3H), 8.0 (s, 3H).

Example 9

The preparation of
N,N-di-(2-[3-(3-hydroxy-2-methyl-4-oxopyrid-1-yl)-propionamido]-ethyl)-2-[3-(3-hydroxy-2-methyl-4-oxopyrid-1-yl)-propionamido]-ethylamine 3-Benzyloxy-1-(2'-succinimyloxycarbonylethyl)-2-methylpyrid-4-one—prepared as described in Example 7—is reacted with tri(2'-aminoethyl)-amine in an analogous procedure to that described in Example 8 for the reaction of the corresponding 1-(2'-succinimylcarbonylmethyl) compound. Working up in an analogous fashion gives N,N-di-(2-[3-(3-benzyloxy-2-methyl-4-oxopyrid-1-yl)-propionamido]-2-[3-(3-benzyloxy-2-methyl-4-oxopyrid-1-yl) propionamido]ethylamine in 45% yield as a thick viscous oil, $\delta$(CDCl$_3$) 2.2 (s, 9H), 2.6 (t, 2H), 3.3 (m, 4H), 4.1 (t, 6H), 4.9 (s, 6H), 6.1 (d, 3H), 7.3 (s, 15H), 7.6 (d, 3H), 8.8 (m, 3H). Hydrogenation of this tribenzyl derivative over palladium/charcoal in ethanol containing 1% v/v acetic acid in an analogous fashion to that described in Example 8 yields the title compound.

Example 10

The preparation of
N-(3-hydroxy-2-oxopyrid-1-ylacetyl)-N-[3-(3-hydroxy-2-oxopyrid-1-ylacetamido)-propyl]-3-(3-hydroxy-2-oxopyrid-1-ylacetamido)-propylamine 3-Benzyloxy-1-succinimylcarbonylmethylpyrid-2-one—prepared as described in Example 4—(2 g) is dissolved in dimethylformamide (50 ml) and a solution of N-(3-aminopropyl)-1,3-diaminopropane in methanol (20 ml) is added and the reaction mixture is allowed to stand overnight. Rotary evaporation yields an orange oil which is extracted with methylene chloride/water. The organic layer is dried, evaporated to dryness and desiccated over $CaCl_2$ to give N-(3-benzyloxy-2-oxopyrid-1-ylacetyl)-N-[3-(3-benzyloxy-2-oxopyrid-1-ylacetamido)-propyl]-3-(3-benzyloxy-2-oxopyrid-1-ylacetamido)-propylamine as an oil in 60% yield; $\delta(d_6DMSO)$ 1.6 (m, 4H), 3.0 (m, 8H), 4.3 (s, 6H), 4.75 (s, 6H), 6.0 (t, 3H), 6.8 (d, 3H), 7.1 (d, 3H), 7.3 (s, 15H), 8.3 (m, 2H). Hydrogenation of this tribenzyl derivative over palladium/charcoal in ethanol containing 1% v/v acetic acid in an analogous fashion to that described in Example 8 yields the title compound as an oil.

Example 11

Partition data on linked 3-hydroxypyridones and their iron complexes

The partition coefficient $K_{part}$, being the ratio (concentration of compound in n-octanol)/(concentration of compound in aqueous phase) on partition between n-octanol and aqueous tris hydrochloride (20 mM, pH 7.4), is measured by spectrophotometry at 20° C. for various of the compounds of the previous Examples and for their iron(III) complexes (at $10^{-4}M$). The solutions of the complexes are either produced, for compound 8, by dissolving the pre-formed complex prepared as described in Example 13, in the aqueous tris hydrochloride or, for compounds 5 and 10, by formation in the buffer in situ by the admixture of a 3:2 or 1:1 molar ratio, respectively, of the linked hydroxypyridone compound:ferric chloride, the pH thereafter being readjusted to 7.4 if necessary. Acid washed glassware is used throughout and, following mixing of 5 ml of the $10^{-4}M$ aqueous solution with 5 ml n-octanol for 1 minute, the aqueous n-octanol mixture is centrifuged at 1,000 g for 30 seconds. The two resulting phases are separated for a concentration determination by spectrophotometry on each. For the metal-free linked hydroxypyridone compounds, the range 220–340 nm is used for concentration determinations whilst for the iron complexes, the range 340–640 nm is used.

Values typical of those obtained are shown in Table 2, the compounds being identified by the same numbering system as that used in Table 1.

TABLE 2

| | Partition coefficients | |
|---|---|---|
| | Partition coefficient $K_{part}$ | |
| Compound | Free compound | Iron complex [$Fe^{III}$-(compound)$_3$] |
| 5 | 0.017 | 0.10 |
| 8 | 0.02 | 0.03 |
| 10 | 0.2 | 0.3 |

Example 12

In vitro tests of iron binding capacity

The linked hydroxypyridone compounds used in this Example were prepared as described in various of the previous Examples and are identified in Tables 3 and 4 below by the same numbering system as that used in Table 1.

(1) Mobilisation of iron from ferritin

Horse spleen ferritin (Sigma) was used without further purification and its iron content was estimated spectrophotometrically at 420 nm. The ferritin solution is phosphate buffered saline (Dulbecco-OXOID, $10^{-6}M$, pH 7.4) was incubated at 25° C. with the compound at $10^{-4}M$ for 6 and 24 hours. Apoferritin (in admixture with ferritin) and the particular linked hydroxypyridone $Fe^{(III)}$ complex were separated by chromatography on Sephadex G10. The absorption spectra of the high and low molecular weight fractions were recorded and the percentage of iron removed from the ferritin was calculated and is reported in Table 3. For comparative purposes, the procedure was repeated using a blank control, and also with the single ring, bidentate compound 1-ethyl-3-hydroxypyrid-4-one (at $10^{-3}M$). In addition, results reported in the literature for similar tests with $1 \times 10^{-3}M$ desferrioxamine (Crichton et al, J. Inorganic Biochem., 1980, 13, 305) and with $6 \times 10^{-3}M$ LICAMS (Tufano et al, Biochem. Biophys. Acta, 1981, 668, 420) are also given in the Table. It will be seen that the linked hydroxypyridone compounds are less effective at removing iron from ferritin than the single ring compounds probably owing to the fact that the size of the iron complexes formed, like those of desferrioxamine and LICAMS, are too large to rapidly penetrate the ferritin pores.

TABLE 3

| Removal of iron from ferritin | | |
|---|---|---|
| | Concentration | Percentage of iron removed |
| Compound | M | 6 hours | 24 hours |
| Control | — | <1 | <1 |
| 1-ethyl-3-hydroxypyrid-4-one | $10^{-3}$ | 25 | 44 |
| 4 | $10^{-4}$ | <1 | 3 |
| 8 | $10^{-4}$ | 3 | 10 |
| Desferrioxamine | $10^{-4}$ | 1.5 | — |
| LICAMS | $6 \times 10^{-3}$ | 0 | — |

(2) Mobilisation of iron from transferrin

Human transferrin (Sigma) was loaded with iron(III) by the method of Bates and Schlaback, J. Biol. Chem. (1973) 248, 3228. $^{59}$Iron (III) transferrin ($10^{-5}M$) was incubated with a $4 \times 10^{-3}M$ solution in tris HCl (0.1M, pH 7.4) of one of various pyridones as indicated in Table 4 for periods of 6 hours. Apotransferrin (inadmixture with transferrin) and the particular linked hydroxypyridone complex ($Fe^{(III)}$ complex were separated by chromatography or Sephadex G10. The $59^{Fe}$ content of both fractions was determined and the percentage of iron removed from transferrin was calculated and is reported in Table 4. For comparative purposes, this procedure was repeated with desferrioxamine and EDTA. It will be seen that three ring compound 8, in particular, gives markedly better results than desferrioxamine or EDTA.

TABLE 3

Removal of iron from transferrin

| Compound | Percentage of iron removed after 6 hours |
| --- | --- |
| 5 | 32 |
| 8 | 40 |
| Desferrioxamine | 17 |
| EDTA | 27 |

Example 13

Preparation of the iron complexes

The iron complex of 1,6-(3-hydroxy-2-oxypyrid-1-ylacetamido)-hexane (compound 4: described in Example 4) is prepared by either procedure (a) or procedure (b).

(a) An aqueous solution of 2 molar equivalents of ferric chloride is reacted for 5 minutes at room temperature with an aqueous solution containing 3 molar equivalents of 1,6-di-(3-hydroxy-2-oxypyrid-1-ylacetamido)-hexane[1]. The resultant solution is adjusted to pH 7.0 using 2 molar aqueous sodium hydroxide and is then freeze dried. The resulting powder is extracted with chloroform, filtered and the filtrate subjected to rotary evaporation to give an essentially quantitative yield of a complex containing the 1,6-di-(3-hydroxy-2-oxopyrid-1-ylacetamido)-hexane bivalent anion and the ferric cation. Recrystallisation of the complex from ethanol gives wine red coloured crystals, m.p. 300° C., $\nu_{max}$ (nujol) 1,520, 1,610 cm$^{-1}$.

[1]The concentration of the linked hydroxypyridone compound is 0.1M although this figure may be varied, for example in a range of 0.01 to 0.05M, being constrained at the upper end of the range by the solubility of the compound in the reaction solvent.

(b) An ethanolic solution of 2 molar equivalents of ferric chloride is reacted for 5 minutes at room temperature with a chloroform solution containing 3 molar equivalents of 1,6-di-(3-hydroxy-2-oxopyrid-1-ylacetamido)-hexane[1]. The resultant solution is neutralised by the addition of solid sodium carbonate, the precipitated sodium chloride removed by filtration and the filtrate evaporated to give an essentially quantitative yield of a complex containing the 1,6-di-(3-hydroxy-2-oxopyrid-1-ylacetamido)-hexane bivalent anion and the ferric cation, m.p. >300° C.

[1]The concentration of the linked hydroxypyridone compound is 0.1M although this figure may be varied, for example in a range of 0.01 to 0.05M, being constrained at the upper end of the range by the solubility of the compound in the reaction solvent.

N,N-[2-(3-hydroxy-2-oxopyrid-1-ylacetamido)-ethyl]-2-(3-hydroxy-2-oxopyrid-1-ylacetamido)-ethylamine (compound 8: described in Example 8) is reacted with ferric chloride in a 1:1 molar ratio by either procedure (a) or (b) above to give the neutral iron(III) containing the N,N-[2-(3-hydroxy-2-oxopyrid-1-ylacetamido)-ethyl]-2-(3-hydroxy-2-oxopyrid-1-ylacetamido)-ethylamine trivalent anion and the ferric cation in 1:1 preparation. This complex is obtained as wine red coloured crystals, m.p. >300° C., $\nu_{max}$ (nujol) 1530, 1580(w), 1620(w) and 1660 cm$^{-1}$.

Example 14

In vitro tests on permeation of iron complexes into human erythrocytes

The accumulation of iron by human erythrocytes which are associated with the iron complexes of three compounds described in earlier Examples was studied by incubating for 1 hour at 37° C. a 5% suspension of erythrocytes in a medium consisting of the $^{59}$Fe labelled iron complex[1] (10$^{-3}$M) in aqueous sodium chloride (130 mM) buffered to pH 7.4 by tris hydrochloride (2 ml). Following this period of incubation, an aliquot of the erythrocyte/medium mixture was placed above a layer of silcone oil and the erythrocytes separated by centrifugation through the oil. The $^{59}$Fe levels associated with the erythrocytes and the incubation medium were then counted. By way of comparison, a similar experiment was concluded with ferric citrate. The results obtained are shown in Table 5 where the amount of the complex entering erythrocytes (n.mole) is given, the quoted values being in each case the mean of at least three determinations. It will be seen that each of the iron complexes compares well with ferric citrate.

[1]The iron complexes of the compounds are prepared in situ in the buffered solution using the compound and Fe$^{59}$Cl$_3$ in exactly similar ratios to those described in Example 13 for compounds 4 and 8, and for compound 5 in the same ratio as described in that Example for compound 4.

TABLE 5

Uptake of complexes by erythrocytes

| Compound | Amount of complex entering erythrocytes (n.mole) |
| --- | --- |
| Fe$^{III}$ complex of compound 4 | 52 |
| Fe$^{III}$ complex of compound 5 | 85 |
| Fe$^{III}$ complex of compound 8 | 45 |
| Fe$^{III}$ citrate | <5 |

Example 15

In vitro tests on permeation of rat jejunal sac by iron complexes

The iron uptake into the serosal space of the inverted rat jejunal sac was compared for the iron complexes of two compounds described in earlier Examples. Rats (male Sprague Dawley, 60 g) were killed and the jejunum removed, everted and cut into three segments (4 cm length). The segments were tied at both ends and filled with Krebs Ringer buffer (0.2 ml) and incubated in Krebs Ringer buffer containing $^{59}$Fe complexes at 37° C. for periods up to 1 hour (the iron complexes were prepared in situ by an analogous procedure to that described in Example 14). The contents of the sac were counted for $^{59}$Fe and measured spectrophotometrically.

The results obtained for the two iron complexes according to the present invention and, by way of comparison, for ferric citrate (this being on iron compounds which is contained in preparations marketed for the treatment of iron deficiency anaemia) are shown in Table 6, the iron uptake for each compound being shown relative to that for ferric chloride as 1. It will be seen that the complexes of the present invention each provide a level of iron uptake which is significantly higher than the level observed for ferric citrate.

TABLE 6

| Compound | Relative Iron Uptake |
| --- | --- |
| FeCl$_3$ | 1 |
| Fe$^{III}$ complex of compound 5 | 15 |
| Fe$^{III}$ complex of compound 8 | 11 |
| Fe$^{III}$ citrate | 2 |

We claim:

1. A method for the treatment of a patient having a toxic concentration of a metal in the body which comprises administering to said patient, in an amount effective to reduce said toxic concentration, a compound containing 2 to 100 rings carrying adjacent hydroxy or oxo groups, said rings being selected from 3-hydroxypyrid-2-ones, 3-hydroxypyrid-4-ones and 1-hydroxypyrid-2-ones and being covalently linked to each other with retention of their adjacent hydroxy and oxy groups and through linking groups which are either wholly of a hydrocarbon nature or which additionally contain one or more of the groups —O—, —S—, —NH—,

—CONH— and —CON<.

2. The method according to claim 1, in which the metal is selected from the group consisting of iron, aluminium, copper, magnesium and plutonium.

3. The method according to claim 1, in which the metal is iron.

4. The method according to claim 1, in which the linked rings are substituted or unsubstituted 3-hydroxypyrid-2-ones and/or 3-hydroxypyrid-4-ones.

5. The method according to claim 4, in which the rings are either unsubstituted apart from linking groups or are additionally substituted only on one or more ring carbon atoms by an aliphatic hydrocarbon group of 1 to 6 carbon atoms.

6. The method according to claim 5, in which the rings are either unsubstituted apart from linking groups or are additionally substituted only on one ring carbon atom.

7. The method according to claim 5, in which the rings are 2-methyl-3-hydroxypyrid-4-one or unsubstituted 3-hydroxypyrid-2-one.

8. The method according to claim 1, in which two, three or four of said rings are linked.

9. The method according to claim 8, in which three of said rings are linked.

10. The method according to claim 1, in which two 3-hydroxypyrid-2-one or two 3-hydroxypyrid-4-one rings are linked through the nitrogen atoms thereof by a group —(CH$_2$)$_n$—, —(CH$_2$)$_a$—NH—(CH$_2$)$_b$—, —(CH$_2$)$_c$—CONH—(CH$_2$)$_d$—NHCO—(CH$_2$)— or —(CH$_2$)$_c$—CONH—(CH$_2$)$_e$—NH—(CH$_2$)$_f$—NHCO—(CH$_2$)$_c$—, wherein n is an integer from 6 to 12, a and b are each separately an integer from 2 to 6, c is an integer from 1 to 5, d is an integer from 2 to 8, and e and f are each separately an integer from 2 to 4.

11. The method according to claim 10, in which c is an integer from 1 to 3 and the size of the third and fourth types of linking group is limited by the requirement that $4 < 2c+d < 12$ and $6 < 2c+e+f < 12$, respectively.

12. The method according to claim 10, in which n is 8 to 10; a and b are each separately 2 to 5; c is 1 and d is 6, or c is 2 and d is 2 or 4; and c is 1, e is 2 and f is 3 or c is 2, e is 2 and f is 2.

13. The method according to claim 1, in which three 3-hydroxypyrid-2-one or three 3-hydroxypyrid-4-one rings are linked through the nitrogen atoms thereof by a group

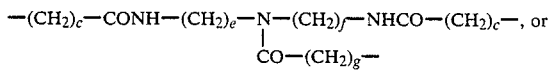

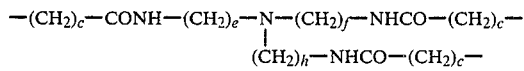

wherein c is an integer from 1 to 5, e and f are each separately an integer from 2 to 4, g is an integer from 1 to 3 and h is an integer from 2 to 4.

14. The method according to claim 13, in which c is an integer from 1 to 3 and the size of the first linking group is limited by the requirement that $6 < 2c+e+f < 12$ whilst the size of the second linking group is limited by the requirement that for each of $2c+e+f$, $2c+e+h$ and $2c+f+h$ the sum is greater than or equal to 6 but less than or equal to 12.

15. The method according to claim 14, in which c is 1, e is 2, f is 3 and g is 1, or c is 1, e is 3, f is 4 and g is 1, or c is 1, e is 3, f is 4 and g is 2; and c=1 and e=f=h=2, or c=2 and e=f=h=2.

16. The method according to claim 1, in which the compound is selected from the group consisting of N-(3-hydroxy-2-methyl-4-oxopyrid-1-ylacetyl)-N-[2-(3-hydroxy-2-methyl-4-oxopyrid-1-ylacetamido)-ethyl]-3-(3-hydroxy-2-methyl-4-oxopyrid-1-ylacetamido)-propylamine, N-(3-hydroxy-2-methyl-4-oxopyrid-1-ylacetyl)-N-[3-(3-hydroxy-2-methyl-4-oxopyrid-1-ylacetamido)-propyl]-4-(3-hydroxy-2-methyl-4-oxopyrid-1-ylacetamido)-butylamine, N,N-di-(2-[3-(3-hydroxy-2-methyl-4-oxopyrid-1-yl)-propionamido]-ethyl)-2-[3-(3-hydroxy-2-methyl-4-oxopyrid-1-yl)-propionamido]-ethylamine, N,N-di-[2-(3-hydroxy-2-oxopyrid-1-ylacetamido)-ethyl]-2-(3-hydroxy-2-oxopyrid-1-ylacetamido)-ethylamine and N-(3-hydroxy-2-oxopyrid-1-ylacetyl)-N-[3-(3-hydroxy-2-oxopyrid-1-ylacetamido)-propyl]-3-(3-hydroxy-2-oxopyrid-1-ylacetamido)-propylamine, and physiologically acceptable salts thereof.

17. The method according to claim 4, in which the compound is administered together with a 3-hydroxypyrid-2-one or 3-hydroxypyrid-4-one substituted on the nitrogen atom thereof by an aliphatic hydrocarbon group of 1 to 6 carbon atoms.

18. The method according to claim 4, in which the compound is administered together with a 3-hydroxypyrid-2-one or 3-hydroxypyrid-4-one substituted on the nitrogen atom thereof by an aliphatic hydrocarbon group of 1 to 6 carbon atoms and on one or more of the ring carbon atoms thereof by an aliphatic hydrocarbon group of 1 to 6 carbon atoms.

19. A method for the treatment of a patient having a toxic concentration of a metal in the body which comprises contacting the patient's blood outside the body with a compound containing 2 to 100 rings carrying adjacent hydroxy and oxo groups, said rings being selected from 3-hydroxypyrid-2-ones, 3-hydroxypyrid-4-ones and 1-hydroxypyrid-2-ones and being covalently linked to each other with retention of their adjacent hydroxy and oxo groups and through linking groups which are either wholly of a hydrocarbon nature or which additionally contain one or more groups, which may be the same or different, selected from —O—, —S—, —NH—,

—CONH— and —CON<, said compound being linked to a support material.

20. The method according to claim 19, in which the metal is selected from the group consisting of iron, aluminium, copper, magnesium and plutonium.

21. The method according to claim 19, in which the metal is aluminium.

22. The method according to claim 1, in which the compound contains 2 to 10 rings.

23. The method according to claim 19, in which the compound contains 2 to 10 rings.

* * * * *

UNITED STATES PATENT AND TRADEMARK OFFICE
CERTIFICATE OF CORRECTION

PATENT NO. : 4,912,118

DATED : March 27, 1990

INVENTOR(S) : HIDER et al

It is certified that error appears in the above-identified patent and that said Letters Patent is hereby corrected as shown below:

On the title page item [75] Inventors: lines 3 and 4 delete "Michael A. Stockham, Saffron Walden"

In the notice regarding disclaimer of term of the patent, delete "Apr. 29, 2006" and replace by --Apr. 29, 2003--.

UNITED STATES PATENT AND TRADEMARK OFFICE
CERTIFICATE OF CORRECTION

PATENT NO. : 4,912,118

DATED : March 27, 1990

INVENTOR(S) : HIDER et al

It is certified that error appears in the above-identified patent and that said Letters Patent is hereby corrected as shown below:

Column 5 line 21 delete "tot he" and replace by --to the--

Column 8 line 40 delete "-($CH_2$-"

Column 8 line 41 delete ")$_i$-$NH_2$" and replace by -- -($CH_2$)$_i$ --

Column 8 line 67 delete "I-($CH_2$-"

Column 8 line 68 delete ")$_n$-I" and replace by -- I-($CH_2$)$_n$-I --

Column 9 line 5 delete "$H_2$N-($CH_2$-"

Column 9 line 6 delete "$_d$-$NH_2$" and replace by -- $H_2$N-($CH_2$)$_d$-$NH_2$ --

Column 9 line 24 delete "-($CH_2$-"

Column 9 line 25 delete ")$_5$-$CO_2$H" and replace by -- -($CH_2$)$_5$-$CO_2$H --

Column 10 line 30 delete "-O-(CH-"

Column 10 line 31 delete "$_2$)$_i$-$CO_2$H" and replace by -- -O-($CH_2$)$_i$-$CO_2$H --

Column 10 line 58 delete "$H_2$N-CH-"

Column 10 line 59 delete "$_2$CONH-($CH_2$)$_2$-NH-($CH_2$)$_3$-NHCOCH$_2$-NH$_2$" and replace by -- $H_2$N-CH$_2$CONH-($CH_2$)$_2$-NH-($CH_2$)$_3$-NHCOCH$_2$-NH$_2$ --

Column 10 line 60 delete "$H_2$H-CH$_2$CONH-($CH_2$)$_2$-N(-"

UNITED STATES PATENT AND TRADEMARK OFFICE
CERTIFICATE OF CORRECTION

PATENT NO. : 4,912,118
DATED : March 27, 1990
INVENTOR(S) : HIDER et al

It is certified that error appears in the above-identified patent and that said Letters Patent is hereby corrected as shown below:

Column 10 line 61 delete "$COCH_2-NH_2)-(CH_2)_3-NHCOCO_2-NH_2$" and replace by -- $H_2N-CH_2CONH-(CH_2)_2-N(COCH_2-NH_2)-(CH_2)_3-NHCOCO_2NH_2$ --

Column 11 line 6 delete "$H_2N-CH-$"

Column 11 lines 7 and 8 delete and replace by
-- $H_2N-CH_2CONH-(CH_2)_2-N(COCH_2CH_2-NH_2)-(CH_2)_3-NHCOCH_2-NH_2$ --

Column 35 line 46 delete "$NHCO-(CH_2)-$" and replace by -- $NHCO-(CH_2)_c$ --

Column 35 line 47 delete

Column 35 line 48 delete "$CO-(CH_2)_c-$" and replace by
-- $-(CH_2)_c-CONH-(CH_2)_e-NH-(CH_2)_f-NH-CO-(CH_2)_c-$ --

Column 36 line 12 delete "$6<2c+e+-$"

Column 35 line 13 delete "$f<12$" and replace by
-- $6<2c+e+f<12$ --

Signed and Sealed this

Fourteenth Day of July, 1992

Attest:

DOUGLAS B. COMER

Attesting Officer      Acting Commissioner of Patents and Trademarks